(12) United States Patent
Briggs et al.

(10) Patent No.: US 6,211,437 B1
(45) Date of Patent: Apr. 3, 2001

(54) NUCLEIC ACIDS FROM MAIZE ENCODING PROTEINS WHICH SUPPRESS PLANT CELL DEATH

(75) Inventors: Steven P. Briggs, Des Monines, IA (US); Gurmukh S. Johal, Columbia, MO (US); John Gray, Cork (IE)

(73) Assignees: Pioneer Hi-Bred International, Inc., Des Moines, IA (US); Curators of the University of Missouri, Columbus, MO (US)

( * ) Notice: Subject to any disclaimer, the term of this patent is extended or adjusted under 35 U.S.C. 154(b) by 0 days.

(21) Appl. No.: 08/810,009

(22) Filed: Mar. 4, 1997

(51) Int. Cl.[7] .............................. A01H 5/00; A01H 5/10; C12N 15/82
(52) U.S. Cl. .................... 800/298; 435/320.1; 536/23.6; 800/278
(58) Field of Search ............................... 435/69.1, 320.1, 435/419, 468; 536/23.6; 800/278, 298

(56) References Cited

U.S. PATENT DOCUMENTS

| | | | |
|---|---|---|---|
| 5,470,359 | 11/1995 | Huffman | 47/58 |
| 5,589,611 | 12/1996 | Briggs et al. | 800/205 |

FOREIGN PATENT DOCUMENTS

| | | | |
|---|---|---|---|
| 0 344 029 | 11/1989 | (EP) | C12N/15/00 |
| WO 95/35318 | 12/1995 | (WO) | |
| WO 97/03183 | 1/1997 | (WO) | |
| WO 98/04586 | 2/1998 | (WO) | |

OTHER PUBLICATIONS

Sugimoto A, et al. "dad–1, an endogenous programmed cell death suppressor in Caenorhabditis elegans and vertebrates." EMBO 14: 4434–4441, 1995.*

Stam M, et al. "The silence of genes in transgenic plants." Ann. Bot. 79: 3–12, 1997.*

Koziel MG, et al. "Optimizing expression of transgenes with an emphasis on post–transcriptional events." Plant Mol. Biol. 32: 393–405, 1996.*

Smith CJS, et al. "Antisense RNA inhibition of polygalacturonase gene expression in transgenic tomatoes." Nature 334: 724–726, Aug. 25, 1988.*

Dangl, Jeffery L., Applications of *Arabidopsis thaliana* to Outstanding Issues in Plant–Pathogen Interactions, International Review of Cytology, 1993, p. 53–83, vol. 144, Academic Press.

Gray et al., *A Novel Suppressor of Cell Death in Plants Encoded by the Lls1 Gene of Maize*, EMBL Sequenece Data Library, Apr. 18, 1997, Heidelberg, Germany, XP002068011, Accession No. U77346.

Newman et al., *Genes Galore: A Summary of Methods for Accessing Results from Large–Scale Partial Sequencing of Anonymous Arabidopsis cDNA Clones*, EMBL Sequence Data Library, Jun. 10, 1997, Heidelberg, Germany, XP002068013, Accession No. U77347.

Newman et al., "Untitled", EMBL Sequence Data Library, Jul. 1, 1997, Heidelberg, Germany, XP002068012, Accession No. 004422.

Caliebe et al., *The Chloroplastic Protein Import Machinery Contains a Rieske–Type Iron–Sulfur Cluster and a Mononuclear Iron–Binding Protein*, The EMBO Journal, vol. 16, No. 24:7342–7350 (1997).

Gray et al., *A Novel Suppressor of Cell Death in Plants Encoded by the Lls1 Gene of Maize*, Cell, 89:25–31 (1997).

Johal et al., *Disease Lesion Mimics of Maize: A Model for Cell Death in Plants*, BioEssays, vol. 17, No. 8, pp. 685–692 (1995).

Johal et al., *A Tale of Two Mimics; Transposon Mutagenesis and Characterization of Two Disease Lesion Mimic Mutations of Maize*, Maydica, 39:69–76 (1994).

Dangl et al., *Death Don't Have No Mercy: Cell Death Programs in Plant–Microbe Interactions*, The Plant Cell, 8:1793–1807 (1996).

* cited by examiner

Primary Examiner—Amy J. Nelson
(74) *Attorney, Agent, or Firm*—Alston & Bird LLP

(57) ABSTRACT

The present invention is drawn to genes from maize encoding proteins which suppress plant cell death and methods of plant transformation therewith.

19 Claims, 9 Drawing Sheets

```
CGTGCGGGGAGAATATGCGCGCGACAATCCCAGCCCTGTCGCTCCTGGTGACGCCGCGGCTCCCCTCGCTCGCCGTGCCGCTGGCTGGAGGCCGCCTCCGCGAGGGCGGTCGTTCTCGGA 120
              M  R  A  T  I  P  A  L  S  L  L  V  T  P  R  L  P  S  L  A  V  P  L  A  G  G  R  L  R  E  G  G  R  S  R
CCCGCCTCCGCGTGGCGGCGCCGACGTCCGTACCAGGGGAAGCGGCGGAGCAGGCGGAGCCGAGCACGTCGGCGCCCGAGTCCGGCGAGAAGTTCTCGTGGAGGGATCACTGGTACCCGG 240
 T  R  L  R  V  A  A  P  T  S  V  P  G  E  A  A  E  Q  A  E  P  S  T  S  A  P  E  S  G  E  K  F  S  W  R  D  H  W  Y  P
TCTCCCTCGTCGAGGACCTCGACCCCAGCCGCCCCACCCCGTTCCAGCTCCTCAACCGGGACCTCGTCATCTGGAAGGAACCCAAGTCCGGCGAGTGGGTCGCGCTCGACGACCGCTGCC 360
 V  S  L  V  E  D  L  D  P  S  R  P  T  P  F  Q  L  L  N  R  D  L  V  I  W  K  E  P  K  S  G  E  W  V  A  L  D  D  R  C
CCCACCGCCTTGCCCCGCTCTCGGAGGGCAGGATCGATGAGACGGGGTGCTTGCAGTGCTCGTATCACGGATGGTCATTCGATGGCTCCGGCGCCTGCACCAAGATCCCCCAGGCCATGC 480
 P  H  R  L  A  P  L  S  E  G  R  I  D  E  T  G  C  L  Q  C  S  Y  H  G  W  S  F  D  G  S  G  A  C  T  K  I  F  Q  A  M
CCGAGGGTCCTGAGGCCCGTGCGGTGCGGTCACCGAAGGCGTGCGCGATCAAGTTCCCCACCCTCGTCTCCCAGGGGCTGCTCTTCGTGTGGCCCGATGAGAATGGGTGGGAGAAAGCGG 600
 P  E  G  P  E  A  R  A  V  R  S  P  K  A  C  A  I  K  F  P  T  L  V  S  Q  G  L  L  F  V  W  P  D  E  N  G  W  E  K  A
CCGCCACCAAGCCTCCAATGTTGCCGAAAGAATTTGAGGACCCGGCCTTCTCCACGGTGACAATCCAGAGGGACTTGTTCTATGGTTATGATACGTTGATGGAGAACGTCTCTGATCCGT 720
 A  A  T  K  P  P  M  L  P  K  E  F  E  D  P  A  F  S  T  V  T  I  Q  R  D  L  F  Y  G  Y  D  T  L  M  E  N  V  S  D  F
CCCATATAGAATTTGCTCACCACAAGGTTACTGGACGAAGAGATAGAGCCAGGCCTTTGACATTCAGGATGGAATCAAGTGGTGCCTGGGGTTACTCAGGAGCAAATTCTGGTAATCCTC 840
 S  H  I  E  F  A  H  H  K  V  T  G  R  R  D  R  A  R  P  L  T  F  R  M  E  S  S  G  A  W  G  Y  S  G  A  N  S  G  N  F
GCATTACTGCAACTTTTGAGGCCCCTTGTTATGCATTGAACAAAATAGAGATAGACACAAAGTTACCCATTTTTGGCGACCAGAAATGGGTCATATGGATTTGCTCTTTCAACATTCCAA 960
 R  I  T  A  T  F  E  A  P  C  Y  A  L  N  K  I  E  I  D  T  K  L  P  I  F  G  D  Q  K  W  V  I  W  I  C  S  F  N  I  P
TGGCCCCAGGGAAGACTCGTTCTATTGTCTGTACCGCTCGAAACTTTTTCCAGTTCACAATGCCAGGAAAAGCATGGTGGCAGCTTGTTCCTCGATGGTATGAACATTGGACTTCAAATT 1080
 M  A  P  G  K  T  R  S  I  V  C  S  A  R  N  F  F  Q  F  T  M  P  G  K  A  W  W  Q  L  V  P  R  W  Y  E  H  W  T  S  N
TGGTCTATGATGGCGATATGATCGTTCTTCAAGGCCAGGAGAAGATTTTCCTAGCTGCAACCAAGGAGTCTTCTACGGATATTAATCAGCAGTACACAAAGATCACATTCACGCCCACAC 1200
 L  V  Y  D  G  D  M  I  V  L  Q  G  Q  E  K  I  F  L  A  A  T  K  E  S  S  T  D  I  N  Q  Q  Y  T  K  I  T  F  T  P  T
AAGCTGATCGATTTGTTTTAGCATTCCGCACATGGCTAAGGAAATTTGGCAATAGCCAGCCGGAGTGGTTTGGAAATCCTACACAAGAAGCATTGCCTTCCACCGTCCTTTCAAAGCGCG 1320
 Q  A  D  R  F  V  L  A  F  R  T  W  L  R  K  F  G  N  S  Q  P  E  W  F  G  N  P  T  Q  E  A  L  P  S  T  V  L  S  K  R
AGATGCTAGACAGATACGAGCAGCACACGTTGAAATGCTCGTCCTGCAAAGGAGCATATAATGCATTCCAGAATCTGCAGAAGGTATTCATGGGAGCGACAGTAGTTTGCTGTGCTGCCG 1440
 E  M  L  D  R  Y  E  Q  H  T  L  K  C  S  S  C  K  G  A  Y  N  A  F  Q  N  L  Q  K  V  F  M  G  A  T  V  V  C  C  A  A
CTGGTATTCCTCCAGATGTTCAGCTCAGGTTATTGATCGGTGCGGCTGCTTTGGTCAGTGCCGCTGTAGCATACGCATTCCATGAGCTCCAGAAGAATTTTGTATTCGTGGATTACGTGC 1560
 A  G  I  P  P  D  V  Q  L  R  L  L  I  G  A  A  A  L  V  S  A  A  V  A  Y  A  F  H  E  L  Q  K  N  F  V  F  V  E  Y  V
ATGCTGACATTGATTCAAAGATTCGTGAGGATCTCTTGTGCGACATCACTGGCTCGCGAGTCGTGTCTGTAGTCTAGGGCTCTAGGCGTCTAGCTAGGGAAAGTAACTTTTTGCCGGCTA 1680
 H  A  D  I  D  .
TAGGTCATATTGCTCACATATGTATTTTGTATAGTGTATGCACTCAACTGTAGCCGATTCAGTGCGAAAATATAGTTTTTATGTTACTATCTATTGGATTAAAATTGTCTCCAGATCCTT 1800
TTAGCATGTAAAATGCCATTTTTCAAATGGAAGTTCTCAATTGCGCCCCTAGACT 1855
```

FIGURE 1

(9) INFORMATION FOR SEQ ID NO.:8:Lls-1 genomic clone
(i) SEQUENCE CHARACTERISTICS: lls-1 promoter sequence
(A) LENGTH: 2822 nucleotides      (C) STRANDEDNESS: Double
(B) TYPE: Nucleotide              (D) TOPOLOGY: Linear
(ii) MOLECULE TYPE: genomic clone
(A) DESCRIPTION: Contains all or substantial part of the lls-1 promoter and corresponds to bp 293 to 3114 of SEQ. ID. No.:2
(iii) HYPOTHETICAL: No
(iv) ANTI-SENSE: No
(v) FRAGMENT TYPE:
(vi) ORIGINAL SOURCE:
(A) ORGANISM: Zea mays            (F) TISSUE TYPE:
(B) STRAIN: maize inbred line B73 (G) CELL TYPE:
(C) INDIVIDUAL ISOLATE:           (H) CELL LINE:
(D) DEVELOPMENTAL STAGE:          (I) ORGANELLE:
(E) HAPLOTYPE:
(vii) IMMEDIATE SOURCE:
(A) LIBRARY: Sau3A maize inbred B73 genomic library
(B) CLONE:
(viii) POSITION IN GENOME:
(A) CHROMOSOME/SEGMENT: 1S
(B) MAP POSITION: Bin 1.01 - 1.03
(C) UNITS:
(ix) FEATURE:
(A) NAME/KEY                      (C) IDENTIFICATION METHOD:
(B) LOCATION:                     (D) OTHER INFORMATION:
(x) PUBLICATION INFORMATION:
(A) AUTHORS:                      (F) PAGES:
(B) TITLE:                        (G) DATE:
(C) JOURNAL:                      (H) DOCUMENT NUMBER:
(D) VOLUME:                       (I) FILING DATE:
(E) ISSUE:                        (J) PUBLICATION DATE
(K) RELEVANT RESIDUES IN SEQ ID NO:8 2822
(xi) SEQUENCE DESCRIPTION: SEQ ID NO.:8:

```
GCAACGCACA CAGACAGGCA GCGATGTCTT TCGCGGGTCA GTAAACCTCA    50
CTCACACAGG CTATTCGTCT TAAGTTTTTT TGTTCAACAT CACATACTTG   100
TGTTGCTAAT GTAACAAAAA AAATTCACAC GCCTCACAAA CATTACAATA   150
TGATTCAAAA TAGACACTAA CCAAACCTTG GAGGACTTTG TACTGGCTAG   200
AGAACACCTA CTCTACTGCT ATGCTGCTTA CCCGAGACAG AGGAAATACA   250
CACGAGCAAC TGTTGTGGAC TTGTTGCAAA ATAGCAAGGA AAGGTATTAG   300
TAATAGCAAG CATAATTGTA GGAGCTGCAA GTATAACAAT GATAGTCTGC   350
TCTTTAGTAC CTTACATGTA TGAAATAAAA AACTATATAG GTAAAGTGAA   400
CAACATGCGT TATGTAAATC TAGCAGACTA TTGGATTGAA AAGAATTCAA   450
TTACAAGGAC AAAGAATGAC TGACGAGGGC AGCAACACAA TAACTAAATG   500
TTCCAAAATG GTCAGATATG AAGGGCTCGA ACGCATGCAC GGCATGATAT   550
GCTAGTTGGG GCCCGTTTCCG TCGGCTTTA AAGATAAGGA AATCTGGATA   600
TGGACTAATG ATGTCTAATT TTTGTTAGAG CCTAGCGCCC TAGCATGCTA   650
ACTAGAAGGT TAATTTTGTT TCTATTTTTT GTTGCACCGA CTGAGCCAAC   700
ATTCTTTTGT CTAGTAGTTT ACATTTTAGT TACTACTCTC TTCGTCTAAA   750
AAGTACTATA TCTCCATTTT TTAAAATGTC TTGCTTTTTG AAGAGCACTA   800
TCTTTTAAAA TCTTGACCAA CTATATAAAA GTACTTCTGA TACATGATAG   850
GTTTAATAAA ATATATAAAA TCTTATATTT TTAGTAAGTC TAGTCAAACT   900
```

FIGURE 2A

```
TAAGAGCTTT TGATGTCGCA CATAGTTGTT TTAAACAAGG TGTTTGTTCA    950
TGTTCGTTCT AATATGTGGA TAGTATTCCG ATTCATTTCG CCAGAGGTGT   1000
GGCTGTGGAT ATTTGGTTAG AGCATCTTCA AGAAAACCCG TAAATCAACT   1050
CCAAAAACGT TTTGAGCCTC CCAACAGTCC CCCTTCCCCT CCCCATATTA   1100
CGCGTCAAGC ATTGTTCCCA ATCGTCCTCT GCGCATGCTG GTtCCcACGT   1150
GTATTTTCCT CGCGCGCAGt TCTGTTGGAG GAGGAAGGCG GGaCGTTGGC   1200
ACTAGCGCTG GCTGGAGATT ATGGCCATCG CAATCAGTTT GTGGCAGTCA   1250
AATGCTTTGT TTTTTGGCC GCTCATGTGA GTATCATTTC TGTGAAAACT    1300
ATCTAAATCA ATATGAATGT ATATTTCTTT AAGTCGTCAC GATAGGAAGA   1350
CTCCATCGTT CTAAAACCTA AACCATGCAC ACATATTCAT CTTTCTCCAA   1400
ACGCAAGTCT CGTGATATTT ATATTCTCGT GCCAGCTAGA TTATCTAGAA   1450
ATTTAGATTC TTAAAAAAAT TCTTTAGAAA AAAAATTATA CCAAACAGGA   1500
CCATGGTTTA AACTATTACG GATAAATAGC ATGACTACCT TAGTATTTAA   1550
ATGATATCAG TTGAAATATG TCGACTTATT TTATAGTTAG TATTATTAGA   1600
ACATGTTTAA ATAATTATCA CATTTAAACC AGATCTACAT ATAAACTATT   1650
TTGCTTGTCA ACTGCATCGC AAACTCACTT GCCTACCATC GGGATCGCGC   1700
TCGTATACAA GTGACACACT TTAAATGATT TAAGCCGCGA AAATTATAAA   1750
TGTACCATCC TCATTTGGCA AGTCTAAAGA TAGCTTTACC ATACAAATGA   1800
AACTAAATTT AAAATTCCAA GTAATAATTA GAAAACTGA TTTGACAGTT    1850
TTTTCAGTAT ATATTAGCA GCTCGCTAAA TCTGAATTTA GAAAGTTTTT    1900
TTGAAATGAG TTGAGATGCT CTTATAATGG TTACTATAGG TTGAGGGACG   1950
GAAGTAGTAG TAGAACTGGT AAACAAATTC GAATTGATC TATTCAACTT    2000
TGTAGCTACT CAGCAAGATG CGAATTGCAA ACATCCGGCG GGGTGGATTC   2050
CGCCACGGCC CACGGGTGGG TTCGTGTCGT TCTCACCGCC GGTCAATCTC   2100
CCCTCCGCGC GGCGCAATTC GTCCGGTGG GGACGGCTAG CTGGCCCAAT    2150
GCCAAAGCTC CACCGACAAA TGCCGCAAAG CGCCATGCGT GGTCGCGTAC   2200
AATTGCCTCC TTCCCCGCCC TTCCTCCCTT CCCTGCCGTG ACGCAACCAC   2250
ACTGCGCTCA CCATCGTGTA CAATGTATTC TCCCTAGCCG AACCGTATCA   2300
GTAGTTCTTA GGGGTGGGCG TTCGGGTTAC CCGAAATTTT CGGGTTGGGT   2350
AATTCAAGTT TTTTAAATTT CGGGTTTTGA GAATCAATAC CCGAAATTAC   2400
AACGGATTTT TCAATACCCG GAATTTCGGG TACCCGGAAT TTCGGGTTCG   2450
GGTTCGGGTA TTCCCAAACT ACCCGAACTA TTGTGTTGGC TTCATAAAAA   2500
CACATACACC CTATTAAATT AGTATAAAAA TATAGTTTGA ATAATGATAT   2550
ACATGGACAT ATAAAACACA AACAATCTAC AATCCCAAGT TATGCACACT   2600
TACACATAAT TATAGATGTA CAAACTTAAA TTATTAAAGC ATGACATGAG   2650
TACATGACAC ATGAAAGCCG GGTAATTCGG GTATTTCGGG TACCCGATTG   2700
TGATACCCGA ATTACCCGAA ATAATTTCGG GTTTTGCAAG TTGCTACCCG   2750
AAATTCCCAA ACAAAATTCG GGTTTCGGGT ATTTCGGGTT CGGGTTCGGG   2800
TATTCCAGGT TTGGGTTTCG GG                                 2822
```

FIGURE 2B

(10) INFORMATION FOR SEQ ID NO.:9: Lls-1 coding region genomic clone
(i) SEQUENCE CHARACTERISTICS:
(A) LENGTH: 4015 nucleotides
(B) TYPE: Nucleotide
(C) STRANDEDNESS: Double
(D) TOPOLOGY: Linear
(ii) MOLECULE TYPE: genomic clone
(A) DESCRIPTION: Contains almost all the coding region of lls-1 from the putative transcriptional start site to a SacI site 45bp 5' of the stop codon predicted from an llsl cDNA. This sequence corresponds to the region between bp 3115 to 7129 of SEQ. ID. No.:2.
(iii) HYPOTHETICAL: No
(iv) ANTI-SENSE: No
(v) FRAGMENT TYPE:
(vi) ORIGINAL SOURCE:
(A) ORGANISM: Zea mays
(B) STRAIN: maize inbred line B73
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

FIGURE 3A (vii) IMMEDIATE SOURCE:
(A) LIBRARY: Sau 3A maize inbred line B73 genomic library
(B) CLONE:
(A) CHROMOSOME/SEGMENT: IS
(B) MAP POSITION: Bin 1.01 - 1.03
(A) NAME/KEY:
(B) LOCATION:
(x) PUBLICATION INFORMATION:
(A) AUTHORS:
(B) TITLE:
(C) JOURNAL:
(D) VOLUME:
(E) ISSUE:
(viii) POSITION IN GENOME:
(C) UNITS:
(ix) FEATURE:
(C) IDENTIFICATION METHOD:
(D) OTHER INFORMATION:

(F) PAGES:
(G) DATE:
(H) DOCUMENT NUMBER:
(I) FILING DATE:
(J) PUBLICATION DATE
(K) RELEVANT RESUDUES IN SEQ ID NO.:9 4015 residues
(xi) SEQUENCE DESCRIPTION: SEQ ID NO.:9:

| | | | | |
|---|---|---|---|---|
| TTACGGGTTT | TTTGCCCAGC | CCTACTAGTT | CTTCCCTCGC | GTTCACTCCC | 50 |
| CAGCGTGGGA | AAATCCCGGA | ATTTTCTTGT | TTGTCCACTG | GTTTTCTTGC | 100 |
| GCCAAAACCA | GGTTTCTCCC | CGTTGCCGTG | GCAGAACTCT | GTTCTTGCCC | 150 |
| AGTCTAGAAG | ATCTGCACCG | TTCCAACCAC | CGACTCCGGC | CGCCAAGCAT | 200 |
| ATAGCCAGCG | CGGCGAAGAA | TTCCAACGC | GAAAGCCAAA | ACCTCTTCAC | 250 |
| TTCACTTCAC | GTCGACACGT | GCGGGAGAA | TATGCGCGCG | ACAATCCCAG | 300 |
| CCCTGTCGCT | CCTGGTGACG | CCGCGGCTCC | CCTCGCTCGC | CGTGCCGCTG | 350 |
| GCTGGAGGCC | GCCTCCGCGA | GGGCGGTCGT | TCTCGGACCC | GCCTCCGCGT | 400 |
| GGCGGCGCCG | ACGTCCGTAC | CAGGGGAAGC | GGCGGAGCAG | GCGGAGCCGA | 450 |
| GCACGTCGGC | GCCCGAGTCC | GGCGAGAAGT | TCTCGTGGAG | GGATCACTGG | 500 |
| TACCCGGTCT | CCCTCGTCGA | GGACCTCGAC | CCCAGCCGCC | CCACCCCGTT | 550 |
| CCAGCTCCTC | AACCGCACC | TCGTCATCTG | GAAGGAACCC | AAGTCCGGCG | 600 |
| AGTGGGTCGC | GCTCGACGAC | CGCTGCCCCC | ACCGCCTTGC | CCCGCTCTCG | 650 |
| GTACGGCGAC | CCGCATCCCT | TCCTCGCCTC | ATCCGTGTCC | TACCGGATCT | 700 |
| CTTCCTCGTT | TCGGCTAATT | TTGGTCTGGG | CATGTGCAGG | AGGGCAGGAT | 750 |
| CGATGAGACG | GGGTGCTTGC | AGTGCTCGTA | TCACGGATGG | TCATTCGATG | 800 |
| GCTCCGGCGC | CTGCACCAAG | ATCCCCCAGG | CCATGCCCGA | GGGTCCTGAG | 850 |
| GCCCGWGCGG | TGCGGTCACC | GAAGGCGTGC | GCGATCAAGT | TCCCCACCCT | 900 |
| CGTCTCCCAG | GGGCTGCTCT | TCGTGTGGCC | CGATGAGAAT | GGGTGGGAGA | 950 |
| AAGCGGCCGC | CACCAAGCCT | CCAATGTGCG | TAGAGTCAGA | CTTTGGACTG | 1000 |
| CGGCTAATTG | GTTGGATTCA | GTTTTGCATT | TCGGTGTCTG | AATTCGATCT | 1050 |
| TATTTGGTTT | CAGGTTGCCG | AAAGAATTTG | AGGACCCGGC | CTTCTCCACG | 1100 |
| GTGACAATCC | AGAGGGACTT | GTTCTATGGT | TATGATACGT | TGATGGAGAA | 1150 |
| CGTCTCTGAT | CCGTCCCATA | TAGAATTTGC | TCACCACAAG | GTACTTGGTA | 1200 |
| CAGTGAGAAA | GCTTAGTTGC | TTGCCACACT | TAAGCACCAT | GATAGTATTT | 1250 |
| TTCAGTTGAA | AGTTGGTGAT | TCGAGGAAAG | ATGTTTTGTT | GCAACCAATT | 1300 |
| TGTGTAGTTT | GCTAAAAAAT | CACCTCCTCA | ATACTGTTTA | ATTGTGTAGG | 1350 |
| CCTCTTATCG | TTTCTGATTG | CCAGTGTGCA | AGTTTAACTA | ACTGTTAGAT | 1400 |
| CTTAACTGTG | GATGTACCCA | TATATTTTTT | TTGCATCATA | GTTTTATTCT | 1450 |
| TTTTTACTTA | TGCTGCATTG | AAATTCCTCA | GAAATGACTT | ATAATGGGCA | 1500 |
| AAAGGGCTGA | ATGGCTGAGT | CTGCCTCTT | ATCGTTTCTA | GATTGCCAGC | 1550 |
| GTGCAAGTTT | AACTAAGGTC | CCGTTTGGTT | TGAGGGATTA | AATATCAGTG | 1600 |
| CCTCCATTTT | AGTCCCATTT | AGTCCATAAA | TTGACAAACG | GTGGGACTAA | 1650 |
| AACAAGGACT | AAACTGTTCT | AGTCTCTAGT | CCCTCAAGGG | ATGACTCTAA | 1700 |
| GGGGCTAAAC | CATAAAAATC | CACTTTTGG | CCCTCCTTCA | TTTCAGTTGC | 1750 |
| ACTAATGGCG | GGAGGATGTT | AAGGAGTATT | TTGGTCTTCT | TATGATTCAT | 1800 |
| TTAATGTGTT | TTGAATACTT | ATAGTTTTTA | GAACCAAACA | GGGAGGGACT | 1850 |
| AAATTTTAGT | CTTCTAACTA | AACTTCGTC | CCTGGACTAA | AGGAACCAAA | 1900 |
| CCCTAACTGT | TAGATCTTAA | CTGTGGATGC | ACCCATATAT | ATTTTTGCAT | 1950 |

FIGURE 3B

```
CATAGTTTTA GTTCTTTTTT ACTTACGCTA CTTGCTTAGT CTGAACAGGC    2000
ATTAATAGGG TGTTTGGTTT GAGGGATTAG TTAGTTCACC CACTCATTCC    2050
TCTTTTCTTT GTTTGGTTTG TTGAATGGAG TAGGTTGGTC AGTGCATTAT    2100
CACATCATTC CTCAGACTAG TAGTTAGTAC TAGTATGAAG AATGGGGTCA    2150
TTCAACCAAA TTTAAGGAAT TGACTCATGA TGCATCACCA CATTTAGAAT    2200
GGAGTGGCTC CTCAAACCAA ACCCTATAAA TGACTGGCTG AGTTAATTGT    2250
GCTATCTGTG TGTCATGAAC TTGTGCCGGC AGCATAGACA AACAAAATGC    2300
TTTATTTTCT CGGGATACAT GGTTTCAGCA AATCCACTCA TGTTTCAGAT    2350
TTTAACTCTT CACAGGTTAC TGGACGAAGA GATAGAGCCA GGCCTTTGAC    2400
ATTCAGGATG GAATCAAGTG GTGCCTGGGG TTACTCAGGA GCAAATTCTG    2450
GTAATCCTCG CATTACTGCA ACTTTTGAGG CCCCTTGTTA TGCATTAAAC    2500
AAGTAAGTTT CAGAAAAGTA CCTGGTCATC TTTGAGTGTG GAGTGATTCT    2550
TATTTACCAC TTAAGCAATT CAGTCGTTAT ACGGTTCTGA ACTTCTGTTA    2600
ACTGGCTTGT ACAGAATAGA GATAGACACA AAGTTACCCA TTTTTGGCGA    2650
CCAGAAATGG GTCATATGGA TTTGCTCTTT CAACATTCCA ATGGCCCCAG    2700
GGAAGACTCG TTCTATTGTC TGTAGCGCTC GAAACTTTTT CCAGTTCACA    2750
ATGCCAGGAA AAGCATGGTG GCAGGTACAT GTGTGTTTAG TGTTTCCTTT    2800
ACTTAAGCTT TGTTTTCCTA TTTGTTTTGT CAACATAATC TTTTAACTGC    2850
TAAAACGAAC TTGTTCTCGC GTTTTTGTGG GAAACAAGGC AAAGGTCCCT    2900
AGTCCCTACT GTAGGCATAT ATTATTGGCA GAGTTTATTA CTTGGTCATG    2950
TTTGAATTTA TATGTGTACA GTCAAATGTT GATAGCTTCT TTCTCTTGGT    3000
GTAGCTTGTT CCTCGATGGT ATGAACATTG GACTTCAAAT TTGGTCTATG    3050
ATGGCGATAT GATCGTTCTT CAAGGCCAGG AGAAGATTTT CCTAGCTGCA    3100
ACCAAGGAGT CTTCTACGGA TATTAATCAG CAGTACACAA AGATCACATT    3150
CACGCCCACA CAAGCTGATC GATTTGTTTT AGCATGCCGC ACGTGGCTAA    3200
GGAAATTTGG CAATAGCCAG CCGGAGTGGT TTGGAAATCC TACACAAGAA    3250
GCATTGCCTT CCACCGTCCT TTCAAAGCGC GAGGTAAAAG CCATCTGGGT    3300
CACCAAAAAA GTTTCAGTAT AATATTTGCT TCAGACATAA AATATCTGAA    3350
TATGACAACC TTTTTGGTGG TCAAAGATCT GTTTTGCTTA CATTCTTAAT    3400
ACTCGATGCA TTGGTAAGTT ATTACAGTTA TCCTTTTTAC TCGATTTTTC    3450
CCTTTCTGAG CAGAACTATT ATCACGTCTT CATTGTTTGT ACACTTGGTT    3500
TCTATGACAC ACAAATTTTT ATTTTACATT ATCAGTTGTC ATATGAACTA    3550
ATGTATTTAC AGCAACCTGC TTAAGTGCTT AGTATCACAA AGGGACAAAT    3600
TCAATGAAAT ATTTGGAAAG ATAGTAGCGT CGAACCACTC TCACAGCTAG    3650
GCATTTGAGA ATAGTTACTT AACTGACAGC GAAGTTCACC TTCTACCGAC    3700
TGGATCTGGA AACAGTATCT TGAAGTAGTT CACACGTAAA CCTTCATCAG    3750
CTGTGTTTCT GGCTTCCAGT AACTCATGTA TTCTTATGAT TGACTTTGTG    3800
TTATGCAGAT GCTAGACAGA TACGAGCAGC TCTCGTTGAA ATGCTCGTCT    3850
TGCAAAGGAG CATATAATGC TTTCCAGAAT CTGCAGAAGG TATTCATGGG    3900
AGCGACAGTA GTTTGCTGTG CTGCCGCTGG TATTCCTCCA GATGTTCAGC    3950
TCAGGCTATT GATCGGTGCG GCTGCTTTGG TCAGTGCCGC TATAGCATAC    4000
GCATTCCATG AGCTC                                         4015
```

FIGURE 3C

Figure 5A
Figure 5B
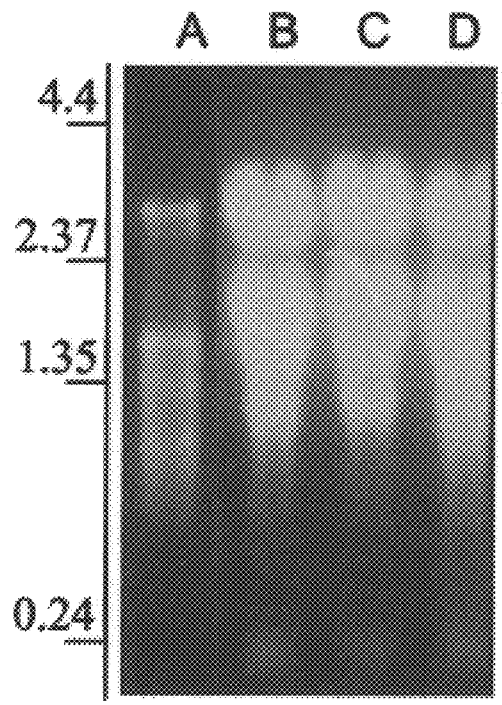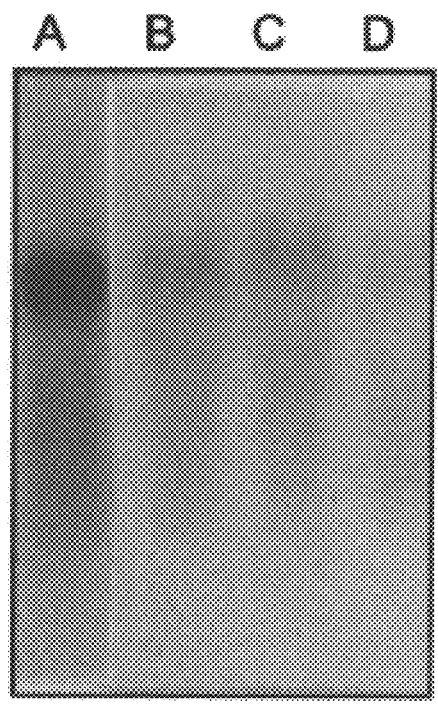
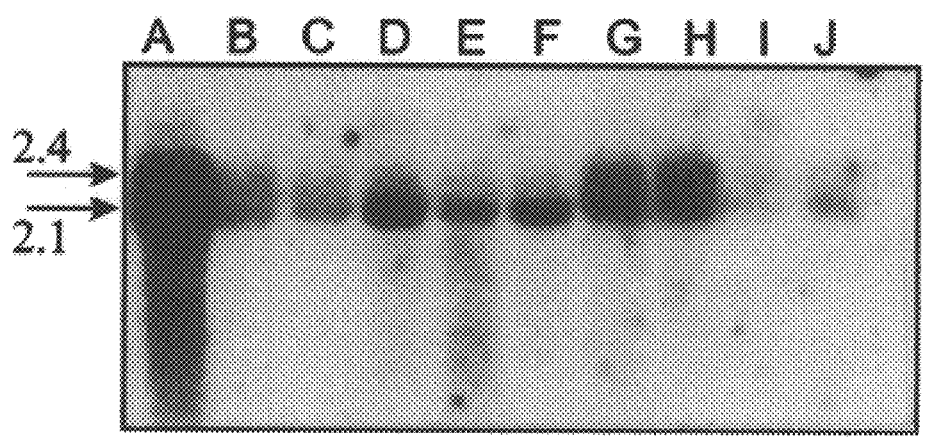
Figure 5C

Figure 6A

```
M MRATIPALSLLVTPRLPSLAVPLAGGRLREGGRSRTRLRVAAPTSVPGEAAEOAEPSTSAPESGEKFSWRDHWYPVSLVEDLOPSRPTPFOLLNRDLVIWKEPKSGEWVA  110
  ::: ::|: ||::|: |:::::: :::: |  ::|:   :   |:||||||||||||||:|||| ||||||| |:  ||||: |||||:||:|
A PIQKDSLFISHHKIPIKGLNFSIKIETFPOPFTRGGAAVLYPLRIRRRRSGSKKNTGGDKEEEGSEFKWRDHWYPVSLVEDLVPNVPTPFOLLGROLVLNFORNOOKWAA  127

M LFYGYOTLMENVSOPSHIEFAHHKVTGRRDRARPLTFRMESSGAWGYSGANSGNPRITATFEAPCYALNKIEIDTKLPIFGDOKWVIWICSFNIPMAPGKTRSIVCSARN  220
  |||||:||||||:|||:| |||||||||||:|  |:  |:: |  | :::|||:||:  |||::||::|:|:|||||:|||||||||||||||||||||||||||||
A LFYGYDTLMENVSDPSHIDFAHHKVTGRRDRAKPLPFKVESSGPWGFOGANDDSPRITAKFVAPCYSMNKIELDAKLPIVGNCKWVIWICSFNIPMAPGKTRSIVCSARN  237

M LDDRCPHRLAPLSEGRIDETGCLOCSYHGWSFDGSGACTKIPOAMPEGPEARAVRSPKACAIKFPTLVSOGLLFVWPOENGWEKAAATKPPMLPKEFEDPAFSTVTIORD  330
   :: ||||||||||||  | :||||||||||:|| | | |||||||||||||:|||||||||||:||||:|||||||| |:: :||  ::||::|||||||||||||
A FOOLCPHALAPLSEGRLDENGHLOCSYHGWSFGGCGSCTRIPOAATSGPEARAVKSPRACAIKFPTMVSOGLLFVWPDENGWORANSIEPPRLPDDFDKPEFSTVTIORD  347

M FFOFTMPGKAWWOLVPRWYEHWTSNLVYDGDMIVLOGOEKIFLAATKESST-DINOOYTKITFTPTOADRFVLAFRTWLRKFGNSOPEWFGN-PTOEALPSTVLSKREML  438
  |||:: ||:||| ||||||||||||||||||:|||||||:||:|:: ||| |:|||||| ||||||||||||:|| ||::||:||||||| :| :||||||:|:|||
A FFOFSVPGPAWWOVVPRWYEHWTSNLVYOGDMIVLOGOEKVFLAKSMESPDYDVNKOYTKLTFTPTOADRFVLAFRNWLRRHGXSOPEWFGSIPSNOPLPSTVLTKAOML  457

M DRYEOHTLKCSSCKGAYNAFONLOKVFMGATVVCCAAAGIPPOVOLRLLIGAAALVSAAVAYAFHELOKNFVFVDYVHADID  520
  ||::|||  |||||||| || |:|:|:||||| ||| |||:|:|||||:|| :|:: ||:|||:||:|||||: | :||:|
A DRFDOHTOVCSSCKGAYNSFOILKKFLVGATVFWAATAGVPSDVOIRLVLAGLSLISAASAYALHEOEKNFVFROYVHSEIE  539
```

Figure 6B

```
                  RIESKE CENTER-BINDING SITE              MONONUCLEAR-IRON-BINDING-SITE
                  Cys-X-His-X16-17-Cys-X2-His             Glu-X3-4-Asp-X2-His-X4-5-His
        R    L              Y  GW                           E
       --C-HM---I-----------C-FHDL-----G-|       |--D----D--H-----H--
       ౼౼౼                    ౼౼                          ౼౼౼౼
       115                   135                          230 234 237  243
       117                   138

NQCHHRGMKLSRDDAGNAKA-PVCTYHGWAHDISGQ      AAEQFCSDMYHAATMSHL    RB1 XylC1
NQCRHRGMRICRSDAGNAKA-PTCSYHGWAYDIAGX      AAEQFCSDMYHAGTTTHL    KF707 BphA1
NQCRHRGMRICRSDAGNAKA-PTCTYHGWAYDIAGN      AAEQFCSDMYHAGTKAHL    KKS102 BphA1
NQCRHRGMRIVRSDGGNAKA-PTCTYHGWAYDIAGN      AAEQFCSDMYHAGTMSHL    B-356 BphA
NQCRHRGMRICRADAGNAKA-PTCSYHGWAYDTAGN      AAEQFCSDMYHAGTTSHL    PpF1 TodC1
NQCRHRGMRICRSDAGNAKA-PTCSYHGWAYDTAGN      AAEQFCSDAYHAGTTSHL    P51 TcbAa
NQCRHRGMRICRADGGNAKS-PTCSYHGWAYDSAGN      AAEQFCSDMYHVGTTSHL    RqF6 BphA1
NQCRHRGMRICRADGGNAKS-PTCSYHGWAYDTGGN      AAEQFCSDMYHAGTTSHL    BD2 IpbA1
NACSHRGAQLLGHKRGNKTT-ITCPYHGWTYNNSGK      TAEN-GRDGYHVSAV-HW    ADP1 BenA
NACSHRGATLCRFRSGNKAT-KTCSFHGWTYSNSGK      QVEN-GADGYHVSTV-HW    pWW0 XylX
NSCRHRGALLCPFSKGNQKF-HVCRYHGWSYDSSGX      QTEN-GLDFYHFGST-HS    AC1100 TftA1
NVCRHRGKTLVSVKAGNAKG-PVCSYHGWGFGSNGX      FAENFVGDAYHVGWT-HA    9816-4 NahAc
NVCRHRGKTLVSAKAGNAKG-PVCSYHGWGFGSNGX      FAENFVGDAYHVGWT-HA    G7 NahAc
NVCRHRGKTIVDAKAGNAKG-PVCGYHGWGFGSNGX      FAENFVGDIYHIGWT-HA    DNT DntAc
SRCPHRGVSL-FKGRVKKGG-LRCVYHGWKFSAKGX      QIEN-GADGYHVGSV-HW    1CBS CbdA
SRCPHRGVSL-FMGRVIKGG-LRCVYHGWKFSAEGX      NLEG-EIDTSHFNFL-HV    Br60 CbaA
XYCPHRRVSL-IYGRNINSG-LRCLYHGWKFDVDGN      ILEG-AIDSAHSSSL-HS    NMH102-2 Pht3
PRCMHRGTSL-TYGHVIKAG-IRCCYHGWLFAVDGT      NWEN-TKDPYHVYIL-HS    POB310 PobA
DFCPHRGAPL-SLGSIQDGK-LVCGYHGLVNDCDGR      MIDN-LKDLTHRTYV-HA    19151 VanA
GYCRHMGGDL-SKGTVKGDE-VACPFHDWRNGGDGR      IIDN-VTDMAHRFYI-HF    H37Rvpht
DACPHRLAPL-SEGRIDETGCLQCSYKGWSFDGSGA      LMEN-VSDPSHIEFAEHK    Zea mays llsl
DLCPHRLAPL-SEGRLDKNGSLQCSYHGWSFGGCGS      LMEN-VSDPSHIDFAEHK    A. thaliana llsl
DQCPHRLAPL-SEGRINKAGQLECPYHGWTFAGSGQ      LMEN-VLDSSHIPYTHHK    PCC6803 slr1747
STCAHRACPL-DLGTVNECR-IQCPYHGWEYSTDGN                            A. thaliana EST
NTCAHRACPL-NLGSVNEGR-IQCPYHGWEYSTDGX                            O. sativa KST
```

DRCPHRLAPLSSGRXDETGCLQCSYHGWSFDGSGA      LMENVSDPSHIEPAHHE    Zea mays llsl
DLCPHRLAPLSEGRLDENGHLQCSYHGWSFGGCGS      LMENVSDPSHIDPAHHE    A. thaliana llsl
DQCPHRLAPLSEGRINKAGQLICFYHGWTPAGSGQ      LMENVLDSSHIPYTHHE    PCC6803 slr1747
```

NUCLEIC ACIDS FROM MAIZE ENCODING PROTEINS WHICH SUPPRESS PLANT CELL DEATH

The invention was made by an agency of the United States Government or under a contract with an agency of the United States Government. Accordingly, the United States Government may have rights to said invention.

FIELD OF THE INVENTION

The invention relates to the genetic manipulation of plants, particularly to novel genes and proteins and their uses in regulating cell death and disease resistance in plants.

BACKGROUND OF THE INVENTION

A host of cellular processes enable plants to defend themselves from disease caused by pathogenic agents. These processes apparently form an integrated set of resistance mechanisms that is activated by initial infection and then limits further spread of the invading pathogenic microorganism.

Subsequent to recognition of a potentially pathogenic microbe, plants can activate an array of biochemical responses. Generally, the plant responds by inducing several local responses in the cells immediately surrounding the infection site. The most common resistance response observed in both nonhost and race-specific interactions is termed the "hypersensitive response" (HR). In the hypersensitive response, cells contacted by the pathogen, and often neighboring cells, rapidly collapse and dry in a necrotic fleck. Other responses include the deposition of callose, the physical thickening of cell walls by lignification, and the synthesis of various antibiotic small molecules and proteins. Genetic factors in both the host and the pathogen determine the specificity of these local responses which can be very effective in limiting the spread of infection.

Many environmental and genetic factors cause general leaf necrosis in maize and other plants. In addition, numerous recessive and dominant genes have been reported which cause discreet necrotic lesions to form. These lesion mutants mimic disease lesions caused by various pathogenic organisms of maize. For example, Les1, a temperature-sensitive conditional lethal mutant, mimics the appearance of *Helminthosporium maydis* on susceptible maize.

Many genes causing necrotic lesions have been reported. The pattern of lesion spread on leaves is a function of two factors: lesion initiation and individual lesion enlargement.

The lethal leaf spot-1 (lls1) mutation of maize is inherited in a recessive monogenic fashion and is characterized by the formation of scattered, necrotic leaf spots (lesions) that expand continuously to engulf the entire tissue. Since lls1 spots show striking resemblance to lesions incited by race 1 of *Cochliobolus* (Helminthosporium) *carbonum* on susceptible maize, this mutation has been grouped among the class of genetic defects in maize called "disease lesion mimics."Lesion mimic mutations of maize have been shown to be specified by more than forty independent loci. These lesion mimic plants produce discreet disease-like symptoms in the absence of any invading pathogens. It is intriguing that more than two thirds of these mutations display a partially dominant, gain-of-function inheritance, making it the largest class of dominant mutants in maize, and suggesting the involvement of a signalling pathway in the induction of lesions in these mutations. Similar mutations have also been discovered in other plants including arabidopsis and barley.

Despite the availability of the large number of lesion mimic mutations in plants, the mechanistic basis and significance of this phenomenon, and the wild-type function of the genes involved, has remained elusive. The understanding of the molecular and cellular events that are responsible for plant disease resistance remains rudimentary. This is especially true of the events controlling the earliest steps of active plant defense, recognition of a potential pathogen and transfer of the cognitive signal throughout the cell and surrounding tissue.

Diseases are particularly destructive processes resulting from specific causes and characterized by specific symptoms. Generally the symptoms can be related to a specific cause, usually a pathogenic organism. In plants, a variety of pathogenic organisms cause a wide variety of disease symptoms. Because of the lack of understanding of the plant defense system, methods are needed to protect plants against pathogen attack.

SUMMARY OF THE INVENTION

Compositions and methods for suppressing cell death and controlling disease resistance in plants are provided. The compositions, cell death suppressing proteins and the genes encoding such proteins, are useful for activating disease resistance, enhancing plant cell transformation efficiency, engineering herbicide resistance, genetically targeting cell ablations, and other methods involving the regulation of cell death and disease resistance in plants.

Additionally, novel promoter sequences are provided for the expression of genes in plants.

BRIEF DESCRIPTION OF THE DRAWINGS

FIG. 1 sets forth the amino acid sequence of the lls1 protein and the DNA sequence encoding the protein. (SEQ ID NOS:2 and 1 respectively)

FIG. 2 sets forth the nucleotide sequence of the lls1 promoter. (SEQ ID NO:3)

FIG. 3 sets forth a maize genomic DNA sequence comprising the lls gene and promoter. (SEQ ID NO:4)

FIGS. 5A–5C show that a single transcript was detected when mRNA from mature leaves was probed with the lls1 transcript.

FIGS. 6A–6C show the preferred sites for possible modification of the protein to alter protein activity. (SEQ ID NOS:2+5–61 respectively)

DETAILED DESCRIPTION OF THE INVENTION

Figure 4:
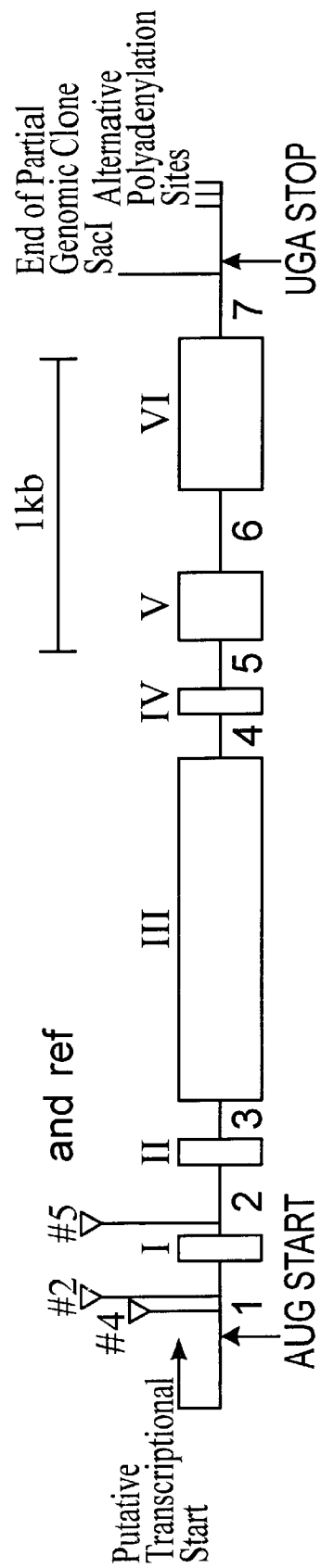
FIG. 4 sets forth the organization of the 3 kb EcoRI restriction fragment containing lls sequence.

The invention is drawn to compositions and methods for controlling cell death and disease resistance in plant cells. The compositions are proteins, ring-hydroxylating dioxygenases, which act to control cell death and regulate disease resistance in plants. The proteins and genes encoding them can be used to regulate cell death and disease resistance in transformed plant cells as well as a variety of other uses. The proteins are useful in resistance to pathogens and survival of the cells particularly after pathogen attack.

One aspect of the invention is drawn to proteins which are involved in the degradation of plant phenolics, cell death-suppressing and disease resistance proteins. Such proteins are characterized by containing two consensus motifs, a Rieske-type iron-sulfur binding site, and a mononuclear iron-binding site, and function as aromatic ring-hydroxylating (ARH) dioxygenases. The Rieske motif contains two cysteine and histidine residues responsible for binding an iron atom cofactor. Plant proteins containing at least one of the motifs have been identified and can be used in the methods of the present invention. Alternatively, proteins from bacteria with the Rieske motif are known in the art and can be used in the methods of the invention. Bacterial proteins of particular interest are ring-hydroxylating dioxygenases, particularly those from the cyanobacterium Synechocystis. See, for example, Gibson et al. (1984) *Microbial degradation of organic compounds*, 181–252. D. T. Gibson, ed. (New York: Marcel Dekker), pp. 181–252.

The cell death-suppressing and disease resistance proteins of the invention encompass a novel class of plant proteins. The amino acid sequence of the lls1 protein isolated from maize is set forth in FIG. 1. However, the proteins are conserved in plants. Thus, as discussed below, methods are available for the identification and isolation of genes and proteins from any plant. Likewise, sequence similarities can be used to identify and isolate other bacterial genes and proteins. The proteins function to inhibit the spread of cell death and control disease resistance in plants. Therefore, the proteins are useful in a variety of settings involving the regulation of cell death and control of disease resistance in plants.

The Rieske motif exhibited by the proteins of the invention is shared by a class of enzymes known as ring-hydroxylating dioxygenases. The motif contains two cysteine and histidine residues responsible for binding an iron atom cofactor—residues that are shared by other proteins termed Rieske iron-sulfur proteins. The bacterial genes included in the proteins of the invention are known as catabolic operons. Thus, it is predicted that the plant proteins are related to the degradation of phenolic compound(s). In fact, a para-coumaric ester accumulates in lls1 lesioned plants, but not in normal-type siblings or wild-type siblings inoculated with the fungus *Cochliobolus heggerostrophus*. While the present invention is not dependent upon any particular mechanism of action, it is believed that the cell death-suppressing function of the novel protein may be mediated by the detoxification of a phenolic compound whose cell damaging effects are fueled by light harvested by photosynthetically-functional pigments in the leaf.

Modifications of such proteins are also encompassed by the present invention. Such modifications include substitution of amino acid residues, deletions, additions, and the like. For example, the protein can be mutagenized in such a way that its activity is reduced, but not completely abolished. See, for example, Jiang et al. (1996), *J. Bacterial*, 178:3133–3139, where the Tyr-221 from the mononucleate iron binding site of toluene dioxygenase was changed to Ala. This change resulted in a reduction in activity to 42% of the normal activity. A change of Tyr-266 to Ala reduced the activity to 12%. In the same manner, amino acid changes, particularly changes from Tyr to Ala, of the sequence of the proteins of the present invention can lead to increases or decreases in activity. FIG. 6 sets forth potential modifications which may alter expression of the resulting protein. Such modifications can result in dominant negative inhibitors of the wild type protein. Using these sequences, the expression of lls1 can be regulated such that disease resistance can be obtained in the absence of lesions.

After each modification of the protein, the resulting protein will be tested for activity. To test for activity, plants can be transformed with the DNA sequence and tested for their response to a fungal pathogen. Of particular interest are changes that result in a reduction of activity. Such changes will confer disease resistance, yet not result in the lesion phenotype. These modified proteins, and the corresponding genes, will be useful in disease defense mechanisms in plants.

Accordingly, the proteins of the invention include naturally occurring plant and bacterial proteins and modifications thereof. Such proteins find use in preventing cell death and controlling disease resistance. The proteins are also useful in protecting plants against pathogens. In this manner, the plant is transformed with a nucleotide sequence encoding the protein. The expression of the protein in the plant prevents cell death and confers resistance to infection by plant pathogens.

The nucleotide sequences encoding the novel proteins are also provided. The lls1 gene from maize encodes the novel maize protein which inhibits the spread of cell death from wounding or internal stresses that occur during photosynthesis. The maize gene can be utilized to isolate homologous genes from other plants, including Arabidopsis, sorghum, Brassica, wheat, tobacco, cotton, tomato, barley, sunflower, cucumber, alfalfa, soybeans, sorghum, etc.

Methods are readily available in the art for the hybridization of nucleic acid sequences. Coding sequences from other plants may be isolated according to well known techniques based on their sequence homology to the maize coding sequences set forth herein. In these techniques all or part of the known coding sequence is used as a probe which selectively hybridizes to other cell death-suppressor coding sequences present in a population of cloned genomic DNA fragments or cDNA fragments (i.e. genomic or cDNA libraries) from a chosen organism.

For example, the entire lls1 sequence or portions thereof may be used as probes capable of specifically hybridizing to corresponding coding sequences and messenger RNAs. To achieve specific hybridization under a variety of conditions, such probes include sequences that are unique among lls1 coding sequences and are preferably at least about 10 nucleotides in length, and most preferably at least about 20 nucleotides in length. Such probes may be used to amplify lls1 coding sequences from a chosen organism by the well-know process of polymerase chain reaction (PCR). This technique may be used to isolate additional lls1 coding sequences from a desired organism or as a diagnostic assay to determine the presence of lls1 coding sequences in an organism.

Such techniques include hybridization screening of plated DNA libraries (either plaques or colonies; see, e.g... Sambrook et al., *Molecular Cloning*, eds., Cold Spring Harbor Laboratory Press (1989)) and amplification by PCR using oligonucleotide primers corresponding to sequence domains conserved among the amino acid sequences (see, e.g. Innis et al., *PCR Protocols, a Guide to Methods and Applications*, eds., Academic Press (1990)).

For example, hybridization of such sequences may be carried out under conditions of reduced stringency, medium stringency or even stringent conditions (e.g., conditions represented by a wash stringency of 35–40% Formamide with 5×Denhardt's solution, 0.5% SDS and 1×SSPE at 37° C.; conditions represented by a wash stringency of 40–45% Formamide with 5×Denhardt's solution, 0.5% SDS, and 1×SSPE at 42° C.; and conditions represented by a wash stringency of 50% Formamide with 5×Denhardt's solution, 0.5% SDS and 1×SSPE at 42° C., respectively), to DNA encoding the cell death suppressor genes disclosed herein in a standard hybridization assay. See J. Sambrook et al., *Molecular Cloning, A Laboratory Manual 2d Ed.* (1989) Cold Spring Harbor Laboratory. In general, sequences which code for a cell death suppressor and disease resistance protein and hybridize to the maize lls1 gene disclosed herein will be at least 50% homologous, 70% homologous, and even 85% homologous or more with the maize sequence. That is, the sequence similarity of sequences may range, sharing at least about 50%, about 70%, and even about 85% sequence similarity.

Generally, since leader peptides are not highly conserved between monocots and dicots, sequences can be utilized from the carboxy terminal end of the protein as probes for the isolation of corresponding sequences from any plant. Nucleotide probes can be constructed and utilized in hybridization experiments as discussed above. In this manner, even gene sequences which are divergent in the aminoterminal region can be identified and isolated for use in the methods of the invention.

Also provided are mutant forms of the lls1 gene (the cell death suppressor and disease resistance gene) and the proteins they encode. Methods for mutagenesis and nucleotide sequence alterations are well known in the art. See, for example, Kunkel, T. (1985) *Proc. Natl. Acad. Sci. USA* 82:488–492; Kunkel et al. (1987) *Methods in Enzymol.* 154:367–382; U.S. Pat. No. 4,873,192; Walker and Gaastra (eds.) *Techniques in Molecular Biology*, MacMillan Publishing Company, N.Y. (1983) and the references cited therein. Thus, the genes and nucleotide sequences of the invention include both the naturally occurring sequences as well as mutant forms. Likewise, the proteins of the invention encompass both naturally occurring proteins as well as variations and modified forms thereof.

The nucleotide sequences encoding the proteins or polypeptides of the invention are useful in the genetic manipulation of plants. In this manner, the genes cf the invention are provided in expression cassettes for expression in the plant of interest. The cassette will include 5' and 3' regulatory sequences operably linked to the gene of interest. The cassette may additionally contain at least one additional gene to be cotransformed into the organism. Alternatively, the gene(s) of interest can be provided on another expression cassette. Where appropriate, the gene(s) may be optimized for increased expression in the transformed plant. Where bacterial ring-hydroxylating dioxygenases are used in the invention, they can be synthesized using plant preferred codons for improved expression. Methods are available in the art for synthesizing plant preferred genes. See, for example, U.S. Pat. Nos. 5,380,831, 5,436,391, and Murray et al. (1989) *Nucleic Acids Res.* 17:477–498, herein incorporated by reference.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein, O., Fuerst, T. R., and Moss, B. (1989) *PNAS USA*, 86:6126–6130); potyvirus leaders, for example, TEV leader (Tobacco Etch Virus) (Allison et al. (1986); MDMV leader (Maize Dwarf Mosaic Virus); *Virology*, 154:9–20), and human immunoglobulin heavy-chain binding protein (BiP), (Macejak, D. G., and P. Sarnow (1991) *Nature*, 353:90–94; untranslated leader from the coat protein mRNA of alfalfa mosaic virus (AMV RNA 4), (Jobling, S. A., and Gehrke, L., (1987) *Nature*, 325:622–625; tobacco mosaic virus leader (TMV), (Gallie, D. R. et al. (1989) *Molecular Biology of RNA*, pages 237–256; and maize chlorotic mottle virus leader (MCMV) (Lommel, S. A. et al. (1991) *Virology*, 81:382–385). See also, Della-Cioppa et al. (1987) *Plant Physiology*, 84:965–968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Towards this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resection, ligation, PCR, or the like may be employed, where insertions, deletions or substitutions, e.g. transitions and transversions, may be involved.

The compositions and methods of the present invention can be used to transform any plant. In this manner, genetically modified plants, plant cells, plant tissue, seed, and the like can be obtained. Transformation protocols may vary depending on the type of plant or plant cell, i.e. monocot or dicot, targeted for transformation. Suitable methods of transforming plant cells include microinjection (Crossway et al. (1986) *Biotechniques* 4:320–334), electroporation (Riggs et al. (1986) *Proc. Natl. Acad. Sci. USA*, 83:5602–5606, Agrobacterium mediated transformation (Hinchee et al. (1988) *Biotechnology*, 6:915–921), direct gene transfer (Paszkowski et al. (1984) *EMBO J.*, 3:2717–2722), and ballistic particle acceleration (see, for example, Sanford et al., U.S. Pat. No. 4,945,050; WO91/10725 and McCabe et al. (1988) *Biotechnology*, 6:923–926). Also see, Weissinger et al. (1988) *Annual Rev. Genet.*, 22:421–477; Sanford et al. (1987) *Particulate Science and Technology*, 5:27–37 (onion); Christou et al. (1988) *Plant Physiol.* 87:671–674 (soybean); McCabe et al. (1988) *BiolTechnology*, 6:923–926 (soybean); Datta et al. (1990) *Biotechnology*, 8:736–740 (rice); Klein et al. (1988) *Proc. Natl. Acad. Sci. USA*, 85:4305–4309 (maize); Klein et al. (1988) *Biotechnology*, 6:559–563 (maize); WO91/10725 (maize); Klein et al. (1988) *Plant Physiol.*, 91:440–444 (maize); Fromm et al. (1990) *Biotechnology*, 8:833–839; and Gordon-Kamm et al. (1990) *Plant Cell*, 2:603–618 (maize); Hooydaas-Van Slogteren & Hooykaas (1984) *Nature* (London), 311:763–764; Bytebier et al. (1987) *Proc. Natl. Acad. Sci. USA*, 84:5345–5349 (Liliaceae); De Wet et al. (1985) In *The Experimental Manipulation of Ovule Tissues*, ed. G. P. Chapman et al., pp. 197–209. Longman, N.Y. (pollen); Kaeppler et al. (1990) *Plant Cell Reports*, 9:415–418; and Kaeppler et al. (1992) *Theor. Appl. Genet.*, 84:560–566 (whisker-mediated transformation); D'Halluin et al. (1992) *Plant Cell*, 4:1495–1505 (electroporation); Li et al. (1993) *Plant Cell Reports*, 12:250–255 and Christou and Ford (1995) *Annals of Botany*, 75:407–413 (rice); Osjoda et al. (1996) *Nature Biotechnology*, 14:745–750 (maize via *Agrobacterium tumefaciens*); all of which are herein incorporated by reference.

The cells which have been transformed may be grown into plants in accordance with conventional ways. See, for example, McCormick et al. (1986) *Plant Cell Reports*, 5:81–84. These plants may then be grown, and either pollinated with the same transformed strain or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved.

As noted earlier, the nucleotide sequences of the invention can be utilized to protect plants from disease, particularly those caused by plant pathogens. Pathogens of the invention include, but are not limited to, viruses or viroids, bacteria, insects, fungi, and the like. Viruses include tobacco or cucumber mosaic virus, ringspot virus, necrosis virus, maize dwarf mosaic virus, etc. Specific fungal pathogens for the major crops include: Soybeans: *Phytophthora megasperma* fsp. *glycinea, Macrophomina phaseolina, Rhizoctonia solani, Sclerotinia sclerotiorum, Fusarium oxysporum, Diaporthe phaseolorum* var. *sojae* (*Phomopsis sojae*), *Diaporthe phaseolorum* var. *caulivora, Sclerotium rolfsii, Cercospora kikuchii, Cercospora sojina, Peronospora manshurica, Colletotrichum dematium* (*Colletotichum truncatum*), *Corynespora cassuicola, Septoria glycines, Phyllosticta sojicola, Alternaria alternata, Pseudomonas syringae* p.v. *glycinea, Xanthomonas campestris* p.v. *phaseoli, Microsphaera diffusa, Fusarium semitectum, Phialophora gregata,* Soybean mosaic virus, *Glomerella glycines,* Tobacco Ring spot virus, Tobacco Streak virus, *Phakopsora pachyrhizi, Pythium aphanidermatum, Pythium ultimum, Pythium debaryanum,* Tomato spotted wilt virus, *Heterodera glycines Fusarium solani*; Canola: *Albugo candida, Alternaria brassicae, Leptosphaeria maculans, Rhizoctonia solani, Sclerotinia sclerotiorum, Mycosphaerella brassiccola, Pythium ultimum, Peronospora parasitica, Fusarium roseum, Alternaria alternata*; Alfalfa: *Clavibater michiganese* subsp. *insidiosum, Pythium ultimum, Pythium irregulare, Pythium splendens, Pythium debaryanum, Pythium aphanidermatum, Phytophthora megasperma, Peronospora trifoliorum, Phoma medicaginis var. medicaginis, Cercospora medicaginis, Pseudopeziza medicaginis, Leptotrochila medicaginis, Fusarium oxysporum, Rhizoctonia solani, Uromyces striatus, Colletotrichum trifolii* race 1 and race 2, *Leptosphaerulina briosiana, Stemphylium botryosum, Stagonospora meliloti, Sclerotinia trifoliorum,* Alfalfa Mosaic Virus, *Verticillium albo-atrum, Xanthomonas campestris* p.v. *alfalfae, Aphanomyces euteiches, Stemphylium herbarum, Stemphylium alfalfae*; Wheat: *Pseudomonas syringae* p.v. *atrofaciens, Urocystis agropyri, Xanthomonas campestris* p.v. *translucens, Pseudomonas syringae* p.v. *syringae, Alternaria alternata, Cladosporium herbarum, Fusarium graminearum, Fusarium avenaceum, Fusarium culmoruim, Ustilago tritici, Ascochyta tritici, Cephalosporium gramineum, Collotetrichum graminicola, Erysiphe graminis* f.sp. *tritici, Puccinia graminis* f.sp. *tritici, Puccinia recondita* f.sp. *tritici, Puccinia striiformis, Pyrenophora tritici-repentis, Septoria nodorum, Septoria tritici, Septoria avenae, Pseudocercosporella herpotrichoides, Rhizoctonia solani, Rhizoctonia cerealis, Gaeumannomyces graminis* var. *tritici, Pythium aphanidermatum, Pythium arrhenomanes, Pythium ultimum, Bipolaris sorokiniana,* Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, *Claviceps purpurea, Tilletia tritici, Tilletia laevis, Ustilago tritici, Tilletia indica, Rhizoctonia solani, Pythium arrhenomannes, Pythium gramicola, Pythium aphanidermatum,* High Plains Virus, European wheat striate virus; Sunflower: *Plasmophora halstedii, Sclerotinia sclerotiorum,* Aster Yellows, *Septoria helianthi, Phomopsis helianthi, Alternaria helianthi, Alternaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthi, Verticillium dahliae, Erwinia carotovorum* pv. *carotovora, Cephalosporium acremonium, Phytophthora cryptogea, Albugo tragopogonis*; Corn: *Fusarium moniliforme* var. *subglutinans, Erwinia stewartii, Fusarium moniliforme, Gibberella zeae* (*Fusarium graminearum*), *Stenocarpella maydi* (*Diplodia maydis*), *Pythium irregulare, Pythium debaryanum, Pythium graminicola, Pythium splendens, Pythium ultimum, Pythium aphanidermatum, Aspergillus flavus, Bipolaris maydis* O, T (*Cochliobolus heterostrophus*), *Helminthosporium carbonum* I, II & III (*Cochliobolus carbonum*), *Exserohilum turcicum* I, II & III, *Helminthosporium pedicellatum, Physoderma maydis, Phyllosticta maydis, Kabatiella zeae, Colletotrichum graminicola, Cercospora zeae-maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvularia pallescens, Clavibacter michiganense* subsp. *nebraskense, Trichoderma viride,* Maize Dwarf Mosaic Virus A & B, Wheat Streak Mosaic Virus, Maize Chlorotic Dwarf Virus, *Claviceps sorghi, Pseudonomas avenae, Erwinia chrysanthemi* pv. *zea, Erwinia corotovora,* Cornstunt spiroplasma, *Diplodia macrospora, Sclerophthora macrospora, Peronosclerospora sorghi, Peronosclerospora philippinensis, Peronosclerospora maydis, Peronosclerospora sacchari, Spacelotheca reiliana, Physopella zeae, Cephalosporium maydis, Caphalosporium acremonium,* Maize Chlorotic Mottle Virus, High Plains Virus, Maize Mosaic Virus, Maize Rayado Fino Virus, Maize Streak Virus, Maize Stripe Virus, Maize Rough Dwarf Virus; Sorghum: *Exserohilum turcicum, Colletotrichum graminicola* (*Glomerella graminicola*), *Cercospora sorghi, Gloeocercospora sorghi, Ascochyta sorghina, Pseudomonas syringae* p.v. *syringae, Xanthomonas campestris* p.v. *holcicola, Pseudomonas andropogonis, Puccinia purpurea, Macrophomina phaseolina, Perconia circinata, Fusarium moniliforme, Alternaria alternate, Bipolaris sorghicola, Helminthosporium sorghicola, Curvularia lunata, Phoma insidiosa, Pseudomonas avenae* (*Pseudomonas alboprecipitans*), *Ramulispora sorghi, Ramulispora sorghicola, Phyllachara sacchari, Sporisorium reilianum* (*Sphacelotheca reiliana*), *Sphacelotheca cruenta, Sporisorium sorghi,* Sugarcane mosaic H, Maize Dwarf Mosaic Virus A & B, *Claviceps sorghi, Rhizoctonia solani, Acremonium strictum, Sclerophthona nmacrospora, Peronosclerospora sorghi, Peronosclerospora philippinensis, Sclerospora graminicola, Fusarium graminearum, Fusarium oxysporum, Pythium arrhenomanes, Pythium graminicola,* etc.

The nucleotide sequences also find use in enhancing transformation efficiency by suppressing cell death in bombarded cells. Thus, the sequences find particular use in transformation methods in which programmed cell death occurs. The physical wounding of particle bombardment triggers programmed cell death. The expression of the cell death-suppressor gene in a bombarded cell serves to inhibit such cell death thereby improving transformation efficiency. By "improving efficiency" is intended that the number of transformed plants recovered by a transformation event is increased. Generally, the number of transformed plants recovered is increased at least two-fold, preferably at least five-fold, more preferably at least ten-fold.

For use in improving transformation efficiency, a cell death suppressor gene is included in an expression cassette. Typically, the gene will be used in combination with a marker gene. Other genes of interest may additionally be included. The respective genes may be contained in a single expression cassette, or alternatively in separate cassettes. Methods for construction of the cassettes and transformation methods have been described above.

As noted, the cell death suppressor gene can be used in combination with a marker gene. Selectable marker genes and reporter genes are known in the art. See generally, G. T. Yarranton (1992) *Curr. Opin. Biotech.*, 3:506–511; Christopherson et al. (1992) *Proc. Natl. Acad. Sci. USA*, 89:6314–6318; Yao et al. (1992) *Cell*, 71:63–72; W. S. Reznikoff (1992) *Mol. Microbiol.*, 6:2419–2422; Barkley et al. (1980) *The Operon*, pp. 177–220; Hu et al. (1987) *Cell*, 48:555–566; Brown et al. (1987) *Cell*, 49:603–612; Figge et al. (1988) *Cell*, 52:713–722; and, Deuschle et al. (1989) *Proc. Natl. Acad. Aci. USA*, 86:5400–5404.

Plant tissue cultures and recombinant plant cells containing the proteins and nucleotide sequences, or the purified protein, of the invention may also be used in an assay to screen chemicals whose targets have not been identified to determine if they inhibit lls1 protein. Such an assay is useful as a general screen to identify chemicals which inhibit lls1 protein activity and which are therefore herbicide candidates. Alternatively, recombinantly-produced lls1 protein may be used to elucidate the complex structure of the enzyme. Such information regarding the structure of the lls1 protein may be used, for example, in the rational design of new inhibitory herbicides. It is recognized that both plant and bacterial nucleotide sequences may be utilized. The inhibitory effect on the cell-suppressor protein may be determined in an assay by monitoring the rate of cell death or alternatively by monitoring the accumulation of the activating phenolic compound, particularly the para-coumaric ester associated with lesion mutants.

If such a chemical is found, it would be useful as a herbicide, particularly if plant or bacterial mutant genes can be isolated or constructed which are not inhibited by the chemical. As indicated above, molecular techniques are available in the art for the mutagenesis and alteration of nucleotide sequences. Those sequences of interest can be selected based on resistance to the chemical. Where resistant forms of lls1 or a corresponding gene have been identified to a chemical, the chemical is also useful as a selection agent in transformation experiments. In these instances, the mutant lls1 would be used as the selectable marker gene.

The sequences of the invention also find use to genetically target cell ablations. In this manner, dominant negative nucleotide sequences can be utilized for cell ablation by expressing such negative sequences with specific tissue promoters. See FIG. 6. For example, stamen promoters can be utilized to drive the negative alleles to achieve male sterile plants. (See, for example, EPA0344029 and U.S. Pat. No. 5,470,359, herein incorporated by reference). Alternatively, cell ablation can be obtained by disrupting dominant negative oligonucleotides with a transposable insertion. In this manner, very specific or general patterns of cell ablations can be created. Additionally, to provide specific cell ablation, antisense oligonucleotides for lls1 or other genes of the invention can be expressed in target cells disrupting the translation which produces the cell death suppressor proteins.

As discussed, the genes of the invention can be manipulated to enhance disease resistance in plants. In this manner, the expression or activity of the lls1 or other cell death suppressor or disease resistance gene can be altered. Such means for alteration of the gene include co-suppression, antisense, mutagenesis, alteration of the sub-cellular localization of the protein, etc. In some instances, it may be beneficial to express the gene from an inducible promoter, particularly from a pathogen inducible promoter. Such promoters include those from pathogenesis-related proteins (PR proteins) which are induced following infection by a pathogen; e.g., PR proteins, SAR proteins, beta-1,3-glucanase, chitinase, etc. See, for example, Redolfi et al. (1983) *Neth. J. Plant Pathol.* 89:245–254; Uknes et al. (1992) *The Plant Cell* 4:645–656; and Van Loon (1985) *Plant Mol. Virol.* 4:111–116.

A promoter which is capable of driving the expression of genes in a plant cell is additionally provided. The promoter is inducible. Thus, it may be manipulated to express heterologous resistance mechanisms at the site of pathogen infection. Accordingly, the promoter is useful for driving any gene in a plant cell, particularly genes which are needed at the site of infection or wounding. That is, the promoter is particularly useful for driving the expression of disease or insect resistance genes. The nucleotide sequence of the promoter is provided in FIG. 2.

It is recognized that the nucleotide sequence of the promoter may be manipulated yet still retain the functional activity. Such methods for manipulation include those discussed above. Thus, the invention encompasses those modified promoter sequences, as well as promoter elements retaining the functional activity of the promoter. Such elements and modified sequences can be assayed for activity by determining the expression of a reporter gene operably linked to the promoter element or modified promoter sequence.

A genomic DNA sequence comprising the lls gene and promoter are provided in FIG. 3. The sequence can be used to construct probes to determine the location and organization of similar sequences in other plants, particularly to analyze the location of other cell death suppressing and disease resistance sequences.

The following examples are offered by way of illustration and not by way of limitation.

EXPERIMENTAL

Materials and Methods

Plant Material

The original lls1 mutant, containing the reference allele, was obtained from the Maize Genetics Coop., University of Illinois, Urbana/Champaign. Stocks containing active Mu transposons were obtained from Dr. D. Robertson, Iowa State University. The six transposon tagged mutant alleles, lls1-1 through lls1-6, were previously designated as lls*-29215, lls*-42230, lls*-1127, lls-*1424, lls*-3744, and lls*-4911, respectively (Johal et al., (1994), *A Tale of Two Mimics; Transposon Mutagenesis and characterization of Two Disease Lesion Mimic Mutations of Maize*, Maydica 39:69–76).

DNA Extraction, RFLP Mapping and Co-segregation Analysis

DNA was isolated by a urea (Dellaporta et al. (1983), *Plant Molecular Biology Reporter* 1:19–22) or CTAB (Hulbert et al. (1991) *Molecular and General Genetics* 226:377–382) extraction protocol. DNA samples (15 to 30) from either mutant or wild-type plants were pooled and digested individually with seven restriction enzymes. Southern blot analysis was performed as described by (Gardiner et al. (1993) *Genetics* 134:917–930) except that UV crosslinking and use of dextran sulfate were omitted. Blots were hybridized systematically with specific probes from different Mu elements. Mapping probes were provided either by the Maize Mapping Project at the University of Missouri or from Pioneer Hi-Bred Int. Inc. Pre-hybridizations and hybridization of southern blots was performed at 65° C. unless otherwise specified. A 3.0 kb EcorRI Mu8co-segregating DNA marker was cloned from an lls1*-5/lls1-ref plant using standard cloning procedures (Ausubel et al. (1994) *Current Protocols in Molecular Biology*). The Zap Express™ vector (Stratagene) was employed and packaging, screening and in vivo excision protocols performed according to manufacturers instructions. The primer sequences (SEQ ID NOS:62–64 respectively) for confirmation analysis were: GSP1: 5' TGG GGA ACT TGA TCG CGC ACG CCT TCG G3', GSP2: 5' TCG GGC ATG GCC TGG GGG ATC TTG G 3', and GSP3: 5' GGC CAC GCG TCG ACT AGT AC 3' (IDT, Coralville Iowa). The thermocycling regime used for confirmation analysis was 94° C. for 5 min, then cycled 40 or 42 times for 30 seconds at 94° C., 1 min and 30 sec at 62° C., and 1 min at 72° C., and finally 5 min at 72° C. Mini-libraries of cloned amplified fragments using the TA Cloning4S vector (Invitrogen) were created and individual colonies for clones with inserts of the appropriate size. A 5' RACE fragment was used to screen a pa405 maize seedling leaf cDNA library and 3 individual clones were recovered and converted to the phagemid form by in vivo excision from the Zap Express™ (Stratagene) vector. Primers GSP1 and GSP2 were used for 5' RACE and GSP3 was used for 3' RACE using 5' and 3' RACE Kits and recommended manufacturers instructions (GIBCO, Md.). To isolate an lls1 genomic clone, a B73 partial SauIIIA library in lambda DashII was screened using a probe from a 3' RACE product spanning the lls1 gene from GSP3 to the polyadenylation site. A single positive clone was recovered and a 7.129 kb SacI fragment was subcloned into pBSKS+ (Stratagene) to create the plasmid pJG201. RFLP mapping of the Arabidopsis lls1 homolog was performed using the Recombinant Inbred (RI) lines generated from a cross between Arabidopsis ecotypes Columbia and Landsberg erecta. 48 RI lines were scored using an EcoRV polymorphism using an lls1 homolog cDNA as probe. The map position was determined on MAPMAKER using the Kosambi mapping function (Lander et al. (1987) *Genetics* 121:174–181).

Primer Extension Analysis

For primer extension analysis of the maize lls1 gene an oligonucleotide complementary to the coding strand in the lls1 gene from 139–173 bases downstream of the predicted first in-frame ATG was synthesized by DNA Technologies, Inc. (Coralville, Iowa). The oligonucleotide (SEQ ID NO:65) GSP17 (5' GTG CTC GGC TCC GCC TGC TCC GCC GCT TCC CCT GG 3') was end-labeled with $^{32}$P. Primer extension analysis was performed by the method described by McKnight et al. (1981), *Analysis of Transcriptional Regulatory Signals of the HSV Thymidine Kinase Gene: Identificatin of an Upstream Control Region*, Cell 25:385–398, except for the following modifications. 40 mg of total RNA from immature tassels of a B73 inbred plant and 0.2 pmol of labeled oligonucleotide were annealed at one of either 33° C., 37° C., 45° C., or 55° C. for 4 hours. Following the extension reaction RNA in the sample was removed by adding 2 µl of 0.5M EDTA and 1u1 of mixed RNAases (0.5 mg/ml RNAase A and 10,000 units/ml RNase T1; Ambion) and incubating at 37° C. for 30 minutes. The primer extension products were separated on a 6% denaturing polyacrylamide sequencing gel and the size of the extension product determined by comparison with a DNA sequence ladder.

Northern Blot Analysis

Total RNA was isolated from leaves of 10 leaf-stage wild-type plants in a population segregating for the Les1O1 mutation, Johal and Briggs (1992) *Science* 258:985–987. mRNA was enriched from total RNA using a magnetic bead affinity protocol (Dynal Inc. Great Nect N.Y.). mRNA was isolated from A632 inbred plants using the MicroQuick protocol (Pharmacia, Piscataway N.J.). Hybridizations were performed either in modified Church and Gilberts solution at 42° C. or in the following hybridization solution at 65° C.–1% casein (Technical Grade, Sigma), 1% calf skin gelatin (225 bloom, Sigma), 0.2% SDS (Mol. Biol Grade, Fisher), 0.1% Sarkosyl (IBI), 5×SSC. Transfer to nylon membrane (Magnacharge MSI, Westboro Mass.) was performed by standard protocols, hybridizations were carried out overnight and blots were washed as indicated in the results section.

DNA Sequencing and Analysis

DNA sequencing was performed by a cycle sequence method using a SequiTherm™ Cycle Sequencing Kit (Epicentre, Madison Wis.) according to the manufacturers protocol. Local sequence comparisons were performed using software including ALIGN and MEGALIGN programs of the DNASTAR software package (DNASTAR Inc. Madison Wis.). Algorithms such as the neighborhood search algorithm BLAST (Autschul et al. (1990), Basic Local Alignment Search Tool, *J. Mol. Biol.* 215:403–410) or BEAUTY (Worley et al. (1995), An Enhanced BLAST-based Search Tool that Integrates Multiple Biological Information Resources into Sequence Similarity Search Results, *Genome Res.* 5:173–184) were employed. Searches of the Genbank databases were performed using the National Center for Biotechnology Information's BLAST WWW Server with links to Entrez and to the Sequence Retrieval System (SRS) provided by the Human Genome Center, Baylor College of Medicine Server at Houston Tex. via Internet access.

Analysis of Light Requirement for lls1 and dd Lesion Development

To determine the spectral range of light required for lesion formation, sections of leaves were clamped between 0.125 inch Plexiglas GM filters held in place by a metal stand with a side arm clamp. The following transparent filters were used: Plexiglas GM 2423 (red), 2711 (Far red), 2424 (blue), 2092 (green), 2208 (yellow), and 2422 (Amber) or Clear, (Cope Plastics Inc. St. Louis. Mo.). Transmission spectra of filters were determined by examining small sections of filters in a spectrophotometer. Leaf sections of greenhouse or field-grown plants were covered in aluminum foil to completely remove incident light. Following complete lesioning of a leaf, filters were removed to observe if lesioning had occurred in the covered region.

The lls1 Mutation is Cell Autonomous and lls1 Lesions Exhibit Altered Phenolic Metabolism and Callose Formation.

The expression of the lls1 phenotype is developmentally programmed: a number of round to elliptical lesions often with concentric rings of dead and dying tissue, begin as small chlorotic flecks near the tip of the first leaf at the three to four leaf stage. While these lesions continue to enlarge and eventually coalesce, new lesions initiate down the leafblade along an age gradient and cover the whole leaf within three to four days. Meanwhile, lesions have already started near the tip of the second leaf. This pattern continues and the plant dies shortly after pollen shed. Although the entire leaf tissue becomes necrotic on lls1 plants, lesions rarely develop on stalks. The lls1 mutation is cell autonomous (i.e., the effect of the gene is confined to the cell in which it is expressed) as exhibited by both revertant sectors (Johal et al. (1994) *Maydica*, 69–76) and forward sectors in that the mutant phenotype does not progress into surrounding wild-type tissue. Lls1 lesions were examined for callose deposition which is frequently associated with response to pathogen infection, wounding or intercellular viral movement (Hammond-Kosack et al. (1996), Resistance Gene-dependent Plant Defense Responses, *Plant Cell* 8:1773–1791). Heavy callousing of all cell types within lesions was observed. At the edge of lesions where cells had not yet collapsed, individual bundle sheath cells were the first cells to exhibit callousing of the plasmodesmatal fields suggesting that the cells were responding to some factor or signal emanating from the dying or dead cells.

Mapping of the lls1 Locus.

The original lls1 allele isolated by Ullstrup and Troyer (Ullstrup et al. (1967) *Phytopathology* 57:1282–1283) was used as the reference allele (lls1-ref). Using a combination of cytogenetic and genetic methods, the lls1 gene was initially mapped to the short arm of chromosome 1 (1S) (Hoisington, (1984) *Maize Genetics Newsletter* 58:82–84). To map the gene at a higher resolution, a new population, in which the progeny segregated 1:1 for homozygous and heterozygous lls1 plants, was generated. A W23 inbred plant was fertilized with the lls1 pollen derived from an lls1-ref/lls1-ref plant, and the resulting progeny (two plants) were backcrossed with the lls1-ref homozygotes. DNA isolated from 16 mutant and 14 wild-type plants was used to examine the linkage with a number of RFLP markers. Three tightly linked RFLP markers were identified which flank the lls1 locus. The RFLP marker Php200603 is about 5 cm distal to lls1, whereas UMC157 is about 8 cm proximal to lls1. The linkage of lls1 with another marker, Php200689, could not be broken with these 30 DNAs. All three of these RFLP markers were invaluable in unequivocally classifying the mutant alleles for co-segregation analyses.

Cloning of the lls1 Locus by Transposon Tagging.

Due to the lack of biochemical information on the lls1 mutation, a transposon tagging method was employed to clone the lls1 gene. This experimental approach allows genes to be cloned solely on the basis of phenotype (Bennetzen et al. (1987), *Proceedings of the UCLA Symposium: Plant Gene Systems and their Biology*. ed, 183–204). Both targeted and non-targeted approaches were employed as outlined by (Johal et al. (1994) *Maydica*, 69–76). For the targeted approach, lls1-ref/lls1-ref plants were used as male parents and crossed with wild-type plants (Lls1/Lls1) from lines active for Mu transposition. All F1 plants were expected to be of wild-type phenotype (Lls1/lls1-ref) unless a Mu insertion or some other mechanism had inactivated the Lls1 allele. Such an event would result in an lls1*/lls1-ref plant (lls1* refers to a mutant allele generated during transposon tagging) with a mutant phenotype. Three plants from approximately 30,000 F1 progeny exhibited the mutant phenotype and one of these died before shedding any pollen. The remaining two plants were crossed as male parents to B73 and Pr1 inbreds and these two new mutants have been designated lls1*-1 and lls1*-2 (11s*-29215 and 11s*-42230, respectively, in (Johal et al. (1994) *Maydica*, 69–76).

A few of the progeny (10 plants) from the outcross of the mutant plants with both inbreds were RFLP genotyped to identify plants which had inherited the mutant allele (lls1*). Two plants containing the mutant allele were self-fertilized, and the F2 progeny so derived were found to segregate for the lls1 phenotype in a 1:3 ratio as expected for a recessive mutation. Two other mutant allele-containing plants from the outcross progeny were backcrossed with the lls1-ref/lls1ref mutants. The resultant progeny segregated 1:1 for mutant (lls1*-1 or -2111sl-ref) versus normal plants (Lls1-B73 or -Prl/lls1-ref) and were used for co-segregation analysis.

For non-targeted mutagenesis, Mu-active stocks were crossed to an inbred line and the resulting progeny was self-pollinated to generate F2 (M2) Mutator populations. With this approach, any recessive mutation generated during the F1 cross can be detected in the F2 generation. From more than 24,000 Mutator F2 families screened, four independent families were identified in which one-fourth of the plants exhibited a phenotype typical of lls1. The four mutant alleles have been designated lls1*-3, lls1*4, lls1*-5 and lls1*-6. A number of wild-type plants from each of these four families were pollinated with the lls1-ref/lls1-ref pollen to determine allelism between these new lls1-like mutants and the original lls1 mutant. The segregation of lls1 mutants in the progeny of most of these crosses confirmed allelism between lls1 and the new mutants. All of these mutants were outcrossed with B73 twice and backcrossed to the lls1ref/lls1-ref mutant to create populations suitable for co-segregation analysis as described above for the targeted mutants.

The next step was to confirm that the Mu elements (there are at least nine of them for Mutator) had caused these new insertional mutations. This step, called co-segregation analysis, involved Southern blot analysis to detect the linkage of a Mu element with the mutant allele in question (Bennetzen et al. (1993) Specificity and Regulation of the Mutator Transposable Element System in Maize, *Crit. Rev. Plant Sci.* 12:57–95). DNA was isolated from phenotypically mutant and wild-type plants from the segregating populations described above for each of the mutant alleles. Following identification of a putative co-segregating element, the analysis was extended employing multiple individual DNA samples digested with an appropriate restriction enzyme. In this manier a 3 kb EcoRI restriction fragment, hybridizing with the Mu8 specific probe was found to co-segregate with 66 DNA samples from the lls1*-5 mutation. This co-segregating fragment was cloned and sequenced revealing the organization indicated in FIG. 4. The DNA sequence of the right (267 bp) flank exhibited significant homology with an Arabidopsis EST of unknown function suggesting that an actual gene was disrupted by the Mu8 insertion. On sequencing the 1344 bp left flanking DNA no significant homology to known DNA sequences was detected and a Mu TIR DNA junction (terminal inverted repeats at each end of Mu elements) was not observed. Using a Mu TIR primer and either an M13 forward or reverse universal primer the left flanking (1344 bp) or right flanking (267 bp) DNA was amplified by PCR and used to probe mutant and wild-type DNA samples of all mutant alleles. This experiment revealed single band polymorphisms in nearly all alleles suggesting that this locus was disrupted in several other alleles.

The occurrence of insertions in the same locus for multiple alleles of the same mutation is considered proof that the correct locus has been tagged. A PCR based approach was used to identify Mu type insertions in the vicinity of the cloned region. The right flanking DNA from the lls1*-5 clone was sequenced as described above and primers designed for extension in each direction. These primers were used in combination with Mu TIR primers to detect amplification products in other mutant allele DNA samples but that were absent in their corresponding wild-type samples. Two such PCR polymorphisms were identified from the targeted allele lls1*-2 and the non-targeted allele lls1*4. These products hybridized strongly on a southern blot with the right flanking DNA from allele lls1*-5 indicating that these amplification products were amplified from the same locus. In addition, the amplification of a smaller (189 bp) gene specific fragment was observed in all the mutant and wild-type DNA samples from all alleles that hybridized with the right flanking DNA of the original lls1*-5 clone. Since all these samples were heterozygous for the lls1-ref allele this result indicated that the lls1-ref mutation had also resulted from a Mu insertion. Nested PCR using a Mu TIR primer and GSP2 was performed to isolate this fragment. All PCR products were directly sequenced using the GSP1 or GSP2 primers as sequencing primer and allowed identification of Mu-type insertions within 246 bp and 292 bp 5' of the insertion site of allele lls1*-5 in allele lls1*-2 and lls1*-4 respectively. It was determined that the lls1-ref allele had a Mu insertion at the same site of insertion as that of allele lls1*-5. Southern analysis using the left-flanking DNA of the lls1*-5 clone revealed that the insertion of a Mu element in the lls1-ref allele was not accompanied by a duplication event showing that the two alleles arose due to independent transposition events (explained below).

The occurrence of four independent Mutator insertions in the same locus in plants with the lls1 phenotype but not their corresponding wild-type siblings constitutes proof that a fragment of the lls1 locus had been isolated. It was observed that a Mu insertion event gave rise to the lls1-ref allele which was believed to arise in a non-Mu active background, suggesting that cosegregation analysis should be attempted with an allele of unknown origin before employing it in a targeted mutagenesis strategy since the occurrence of an insertion in the same region of the gene could obfuscate co-segregation analysis with a new allele.

The lls1 Locus Encodes a Novel Plant Protein

To characterize the lls1 locus fully a cDNA and genomic clone was isolated. Gene specific primers GSP1 and GSP3 were employed along with universal primers to amplify 5' and 3' fragments respectively of the lls1 transcript from a cDNA library constructed from 2 week old inbred PA405 seedlings. A 5' fragment was then used as a probe to screen the PA405 cDNA library and 3 individual clones were recovered and the longest phagemid named pJG200 was sequenced (Genbank Acc. # U77345). This sequence was used to screen a maize EST database and another lls1 cDNA with an additional 180 bp at the 5' end was recovered. The combined sequence of these two cDNAs is shown in FIG. 1 and a 521 amino acid continuous open reading frame can be predicted from this partial transcript (FIG. 1). The identification of the termination codon was supported by a similarly located predicted termination codon in the sequence of an Arabidopsis lls1 homolog (below). A primer designed against 139 bp to 173 bp downstream of the predicted start codon of this sequence (GSP 17) was used for primer extension analysis and a 454 bp long primer extension product was observed thus predicting a 2119 bp total length transcript for the lls1 gene. In addition, the 3' ends of the cDNAs and the 3' ends of the three PCR-amplified 3'-ends were also sequenced and three different polyadenylation sites determined thus allowing for variation in the size of the full length transcript (FIG. 1 and 4).

A 3' fragment of the lls1 gene was utilized to screen a partial Sau3A genomic library of the maize inbred line B73 in order to isolate a full-length lls1 gene sequence and a single positive clone (designated G18) was isolated. A 7129 bp SacI fragment was subcloned from the G18 genomic clone and the resulting plasmid named pJG201 was entirely sequenced (Genbank Acc# U77346). By comparison with the cDNA sequence pJG201 was found to contain almost the entire lls1 coding region and a 5' region likely to include the entire promoter. The predicted genomic organization of the lls1 gene (FIG. 4) includes 7 exons and 6 introns. The SacI restriction site at bp 7129 is 45 bp upstream of the predicted stop codon and 320 bp upstream of the polyadenylation sites. Providing that there are no other introns in the 5' region of the gene the predicted transcriptional start site of the lls1 gene occurs at bp 3115 of the 7129 bp subclone.

Southern hybridization suggests that the lls1 gene is single copy in the genome of maize since only one band was observed on Southern blots of the wild-type DNA samples of the lls1-ref allele cut with several restriction enzymes. That a duplicate of the lls1 gene exists has not yet been determined using lower stringency washes. Three bands were observed in lls1*-5 when the EcoR1 digested mutant samples were probed with the left flank. A 10 bp direct repeat was not observed on each side of the Mu8 insertion in allele lls1*-5. These results suggested that a rearrangement of DNA more complex than a simple Mu8 element insertion had occurred at this locus and the nature of this rearrangement was determined by comparison with the genomic sequence of the lls1 gene. The left flanking DNA comprises a direct repeat of the lls1 genomic sequence extending from the EcoR1 site of Intron II to bp 43 of exon 4.

The predicted lls1 protein exhibits a largely hydrophilic protein with a pI of 7.5. No hydrophobic regions suggesting membrane association were observed. This fact suggests a cytosolic or plastidic subcellular location for the LLS 1 protein.

The lls1 Gene Exhibits Tissue and Cell Specific Expression

The lls1 phenotype is developmentally expressed as described above. LLS1 appears to be needed in expanded leaves but not in very young leaves and thus lls1 transcripts may accumulate in older leaves if the gene is transcriptionally regulated. The expression of lls1 in fully expanded leaves of normal plants was examined using a partial cDNA probe that extends from the beginning of exon 2 to the end of the lls1 transcript. A weak signal was detected using 20 pg of total RNA and a high stringency wash. There did not appear to be a significant gradient in gene expression from three successively older leaves. When mRNA derived from pooled total RNA from these leaves was utilized a single transcript was readily detected (FIG. 5). The size of this single transcript was estimated at 1.9±0.2 kb a figure which coincides closely with the full-length size determined by primer extension analysis (1.129 kb). To further examine the developmental pattern of lls1 gene expression, mRNA derived from various plant tissues was probed with an 802 bp NotI/PstI fragment that extends from the end of exon 2 to exon 7 (FIG. 4). Lowest levels of expression were seen in seedling leaves, 3 week old embryos and in young tassels. The lls1 transcript was readily detected in more mature tassels, young and old ear shoots and 1 week old embryos. Surprisingly, the lls1 transcript was most readily detected in seedling roots where the lls1 phenotype has not been observed. In addition, the presence of a second larger transcript (approximately 2.4 kb) was observed that hybridizes with the lls1 probe in seedling roots and older tassel tissue. When observed this larger transcript seems to be expressed in equivalent amounts to the lower transcript. Since genomic blots have indicated that lls1 is a single copy gene, the larger transcript may represent post-transcriptional regulation of lls1 although there is precedence for a northern blot to reveal the existence of a second gene when a southern analysis failed to do so. These results indicate that the lls1 gene is not expressed constitutively in all tissues but exhibits tissue specific transcriptional regulation.

The lls1 Gene is Conserved Between Monocot and Dicot Plants

To determine if lls1 related genes are present in other species or organisms the predicted lls1 protein sequence was utilized to search public databases of sequences of both known and unknown functions. As indicated above, significant homology (70% nucleic acid identity) was observed between the right flanking DNA of lls1*-5 and an expressed sequence tag (EST) from *Arabidopsis thaliana*. (Genbank Acc. # T45298). Three other Arabidopsis ESTs were identified that overlap with this EST (Genbank Acc. #s N37395, H36617 and R30609). The four overlapping ESTs were obtained from the ABRC (Columbus, Ohio) and further sequenced. These sequences were organized into a single contig 1977 bp in length (Genbank Acc. # U77347). The 3' end of this contig overlaps with the upstream region of the rpl9 gene (a nuclear encoded plastid ribosomal protein) ending only 109 bp upstream of the rpl9 transcriptional start. The Arabidopsis contig that exhibits 71.6% amino acid similarity over a 473 consensus length with the maize lls ORF from the available maize cDNA sequence. The amino terminus of the maize versus the Arabidopsis ORFs differ significantly indicating the possibility that each protein has a different leader peptide or that an alternative start codon is utilized. The maize lls1 sequence has therefore been utilized to detect a highly homologous gene from a dicot plant. This result prompted us to map the Arabidopsis contig and this was achieved using the recombinant Inbred (RI) lines developed by Clare Lister and Caroline Dean at the John Innes Center (Lister et al. (1993) *Plant Journal* 4:745–750). Following identification of a suitable polymorphism one EST (Acc# T45298) was used as a probe to score 48 RI lines. The map position was located on the lower arm of chromosome three between GL1 and m249. Importantly, the acdl mutation, whose cell death phenotype is reminiscent of the maize lls1, also maps in this region (Greenberg et al. (1993) Arabidopsis Mutants Compromised for the Control of Cellular Damage During Pathogenesis and Aging, *Plant J.* 4:327–341) suggesting that these two mutations in maize and Arabidopsis are homologous. As genomes from two divergent plant species have been found to have related lls1 genes, it is likely that any number of plant species will possess genes regulating cell survival in a manner similar to the maize lls1 gene. To further test this hypothesis we tested the linkage of maize lls1 and flanking markers to a sorghum mutation named drop-dead-l (dd-1) that is an EMS induced lesion-mimic mutation with spreading lesions highly reminiscent of lls1 lesions. A segregating mapping population was created by crossing a dd/dd line with Shangai Red DD/DD and the progeny were allowed to self. Plants segregating for drop-dead were identified and DNA isolated from several mutant and wild-type progeny. A polymorphism for the lls1 locus could not be identified but a polymorphism for the probe PIO200640 which is ~33 cM distal to lls1 was identified with HindE. This polymorphism showed complete segregation with 14 mutant and 16 wild-type progeny strongly suggesting that this mutation maps to a region syntenic with lls1 and that lls1 and dd are homologous mutations and possibly orthologs.

lls1 Lesions are Induced by Wounding and in les101/lls1 Double Mutants

In addition to intrinsic, developmental signals, external factors also affect lls1 expression. lls1 lesions normally appear randomly on developmentally competent areas of the leaf. However, lls1 lesions can also be triggered to initiate at any site (provided that the tissue is developmentally competent) by killing cells either by inducing an HR with an incompatible pathogen or by physical means (making pin prick wounds). The additive phenotype of the double mutant of lls1 with Les2 or Les*-101 (two dominant mimics that can initiate numerous lesions on maize leaves before they become developmentally competent to express lls1 further supports these results. On the double mutants, the early phenotype of the lesions is discrete and of the respective Les type and also of higher density as compared to that of lls1 lesions. However, as the tissue acquires developmental competence to be able to express the lls1 phenotype, most, if not all, Les sites transform into lls1 lesions that expand in an uncontrolled fashion to consume the whole leaf. Thus the internal metabolic upset and cell death events associated with a Les*-101 lesion appear to act as a trigger for lls1 lesions.

Light is Required for lls1 and dd Lesion Formation

These observations fully support the hypothesis that lls1 functions to contain cell death from spreading, and it appears to be critical during late stages of plant development. Interestingly, the expression of lls1 lesions is completely dependent on light. The region in the center of the leaf was covered with aluminum foil just as lesions were initiating at the tip of the leaf. The lesions formed progressively down the leaf but not where the leaf was protected from light. Aluminum foil also protected lesions induced by pin-prick wounding in maize lls1 plants and also observed clearly in sorghum drop-dead plants. Using plastic filters that transmit different wavelengths of light, it was found that visible light in the spectral region of 650–700 nm is sufficient for this effect. Yellow and orange filters also transmitted some red light in the 650–700 nm so a contribution from light in the 560 to 640 nm range cannot be excluded. Lesions did not form when only blue, green, or far-red light reached the leaf. This phenomenon suggested that active photosynthesis, which harvests light pre-dominantly in the red spectral region, is required for lesion formation. This was addressed genetically by creating double mutants of lls1 with iojap 1 (ijl- a recessive mutation in maize that produces albino and light green sectors on an otherwise normal green leaf) or ncs7 which also exhibits light green but not albino sectors. These double mutants have revealed that lls1 lesions can only form in dark green tissues. This result indicates that some activity related to light harvest or photosynthesis may be important in the initiation and spread of lesions. Double mutants of lls1 with oil yellow-700 provide further support to this interpretation. Oyl- is a dominant mutation which by virtue of its inability to convert protoporphyrin IX to Mg-protoporphyrin, is completely devoid of chlorophyll b and has also reduced levels of chlorophyll a. On oy/+lls1/lls1 plants lesions initiate with a lower density and propagate very slowly in these plants and often lethality does not ensue. Intriguingly, the suppressible effect of oyl on lls1 is not observed when the plants are grown in a greenhouse or growth chamber. Also we have observed that on an lls1/ijl double mutant, where lesions do not initiate or develop in albino tissue, the 'death' signal (that probably allows lls1 lesions to propagate) can sometimes diffuse across (traverse) the albino tissue if the sector is narrow. This suppression is in contrast with many other lesion mimics such as the dominant lesion mimic Les4 which readily forms lesions in the albino sectors of Les4/+ij/ij plants. These observations indicate that a process or a metabolite, which is partly diffusible and whose activity may be affected by factors including light, wounding, and pathogen invasion, is responsible for the initiation and spread of cell death associated with lls1 lesions.

The Predicted LLS1 Protein Contains Two Structural Motifs Highly Conserved in Baterial Phenolic Dioxygenases While no definite function could be ascribed to lls1 from homology searches, analysis of the predicted amino acid sequence of the lls1 gene product has revealed two conserved motifs, a consensus sequence (SEQ ID NO:6) (Cys-X-His-$X_{16-17}$-Cis-$X_2$-His) for coordinating the Reiske-type [2Fe-2S] cluster (Mason and Cammock (1992) The Electron-Transport Proteins of Hydroxylating Bacterial Dioxygenases, *Annu. Rev. Microbiol.* 46:277–305) and a conserved mononuclear non-heme Fe-binding site (SEQ ID NO:7) (Glu-$X_{3-4}$-Asp-X2-His-$X_{4-5}$-His) (Jiang et al. (1996) Site-directed Mutagenesis of Conserved Amino Acids in the Alpha Subunit of Toluene Dioxygenase. Potential Mononuclear Nonheme Iron Coordination Sites, *J. Bacteriol.* 178:3133–3139), which are present in the α-subunit of all aromatic ring-hydroxylating (ARH) dioxygenases involved in the degradation of phenolic hydrocarbons. In addition, the spacing (~90 amino acids) between these motifs, which has recently been shown to be conserved in all ARH dioxygenases, is precisely maintained in LLS1, adding further evidence that LLS1 may encode a dioxygenase function. The ARH dioxygenases consist of 2 or 3 soluble proteins that interact to form an electron transport chain that transfers electrons from NADH via flavin and iron-sulfur (2Fe-2S) redox centers to a terminal dioxygenase. The latter, which is also a multimeric enzyme consisting of either α homomers or α and β heteromers, catalyzes the incorporation of two hydroxyl groups on the aromatic ring at the expense of dioxygen and NAD(P)H.

The consensus sequence of both the Rieske- and iron-binding motifs (SEQ ID NOS:6–7 respectively) as well as the spacing between them are precisely conserved in a hypothetical protein (translated from an ORF) from Synechocystis sp. PCC6803, which in addition, exhibits 66% amino acid identity to LLS1 among a stretch of more than 100 amino acids. Additionally, the Rieske center-binding site has also been detected in the partial sequence of two seemingly related ESTs (SEQ ID NOS:31–32 respectively) of unknown function, one each from rice and Arabidopsis.

lls1 and *Cochliobolus carbonum*

Inoculation of lls1 leaves with *Cochliobolus carbonum* Race 1 causes a proliferation of lls1-type necrotic lesions in the middle to upper parts of the leaves. These lls1-type lesions superficially resemble *C. carbonum* lesions but they are sterile. That is, plating explants on carrot agar medium does not usually yield any *C. carbon* fungal growth. Spontaneous lls1 lesions occurring without inoculation are also sterile and appear similar. Thus the lesions induced by *C. carbonum* inoculation are apparently lls1-type lesions and not susceptible *C. carbonum* lesions. This raises the question as to whether these lesions indicate that the lls1 mutant is susceptible to *C. carbonum* or not. It seems likely that the lls1 plants are resistant to *C. carbonum*, but that *C. carbonum* is able to trigger lls1 lesion formation. The *C. carbonum* could be acting as a stress that sets off the lls1 lesion development. After all, even abiotic stresses, such as needle pricking, will also induce lls1 lesion formation.

Inoculation of lls1 leaves with *Cochliobolus carbonum* toxin plus or toxin minus causes few if any lesions to form in the middle to lower parts of the inoculated leaves. This observation is interpreted to mean that the lls1 mutation possesses induced resistance to *C. carbonum* in that area of the leaf. While both spontaneous lls1 lesions and *C. carbonum* lesions physically resemble each other, neither type was seen in this area of the leaf. In the middle transitional area there are some nascent smaller lls1 lesions. It appears as though only the upper acropetal areas of the leaf at this stage of development, are capable of forming spontaneous lls1 lesions or *C. carbonum* induced lesions.

In the lower-middle areas of lls1 leaves without any pathogen inoculation, a several fold elevation of PR1 and chitinase proteins was observed on western blots over that of Lls1/lls1 wildtype heterozygotes. Upon inoculation, the PR1 and chitinase expression in this area of the leaves was elevated slightly in lls1 and substantially in the Lls1/lls1 heterozygotes, such that after inoculation both lls1 and the wildtype heterozygotes have similar levels of PR1 and chitinase. Thus it appears that: 1) elevated PR gene expression is correlated with resistance to *C. carbonum* in the lower middle area of the leaves, and 2) the PR gene induction exists prior to the resistance.

lls1 and *Cochiobolus heterostrophus*

As was seen with *C. carbonum*, inoculation of lls1 leaves with *Cochiobolus heterostrophus* also causes a proliferation of lls1-type necrotic lesions in the middle to upper parts of the leaves. These lls1-type lesions are generally distinguishable from *C. heterostrophus* necrotic lesions. These lls-type lesions are also sterile; that is, plating explants on carrot agar medium does not usually yield any *C. heterostrophus* fungal growth. Spontaneous lls1 lesions occurring without inoculation are also sterile and appear similar. Thus the lesions induced by *C. heterostrophus* inoculation are apparently lls1-type lesions and not susceptible *C. heterostrophus* lesions. It appears that *C. heterostrophus* triggers formation of lls1 lesions. *C. heterostrophus* appears to be acting as a stress that sets off the lls1 lesion development. After all, even abiotic stresses, such as needle pricking, will also induced lls1 lesion formation.

Inoculation of lls1 leaves with *Cochliobolus heterostrophus* causes few if any lesions to form in the middle to lower parts of the inoculated leaves. This observation was interpreted to mean that the lls1 mutation possesses induced resistance to *C. heterostrophus* in that area of the leaf. Spontaneous lls1 lesions and *C. heterostrophus* lesions are usually distinguishable by appearance, yet neither type was observed in this area of the leaf. In the middle transitional area there are some nascent smaller lls1 lesions, so it appears as though only the upper acropetal areas of the leaf are capable of forming lls1 lesions. However, the lack of *C. heterostrophus* lesions in this area of the leaf relative to their appearance in Lls1/lls1 and Lls1/Lls1 wildtype controls, indicates that lls1 possesses resistance to *C. heterostrophus* in that area of the leaf. That the lls1 heterozygotes are not resistant indicates that this resistance, like lls1 lesion formation, is a recessive Mendelian trait.

In the lower-middle areas of lls1 leaves without any *C. heterostrophus* inoculation, a several fold elevation of PR1 and chitinase proteins was observed on western blots over that of Lls1/lls1 wildtype heterozygotes. Upon inoculation with *C. heterostrophus*, the PR1 and chitinase in this area of the leaves is elevated slightly in lls1 and substantially in the Lls1/lls1 heterozygotes, such that after inoculation they have similar levels of PR1 and chitinase. Thus it appears that elevated PR gene expression is correlated to resistance to *C. heterostrophus* in the lower middle area of the leaves, and that this elevated PR gene expression occurs prior to the inoculation and resistance.

lls1 and *Puccinia sorghi* (Rust)

Rust inoculation of lls1 plants does not necessarily induce lls1-type necrotic lesions. It was observed that rust will infect lls1 plants and produce sporulating lesions. This indicates that unlike *C. carbonum, C. heterostrophus,* and *Puccinia sorghi*, rust, a biotrophic pathogen, is able to infect lls1 and Lls/lls1 heterozygote control plants, The fact that *P. sorghi* will infect and form lesions indicates that *P. sorghi* can evade triggering lls1 lesions formation and that it can survive and grow on lls1. The lls1 mutation is therefore not necessarily rust resistant. Differences that may exist in rust susceptibility in the acropetal versus basipetal regions of the leaf have not been investigated.

Western blots revealed that mutant lls1 plants and Lls1/lls1 wildtype heterozygote plants had similar levels of chitinase expression following rust inoculation. The expression of PR1, however, was slightly higher in the wildtype plants than in lls1 mutants following rust inoculation. These experiments seem to indicate that although rust is able to avoid triggering lls1-type lesions formation in lls1, it still manages to trigger at least chitinase expression. These results may have important ramifications for understanding how pathogens are detected by the plant host, and if detected, whether by the same or different mechanisms, how the signaling pathways determine whether PR gene expression activated.

To date no studies have isolated a protein(s) or gene(s) ubiquitously involved in the degradation of plant phenolics. Phenolics in plants are often sequestered in cell compartments until needed or synthesized only when required. Some phenolics however such as benzoic acid and salicylic acid have been proposed to play key roles in preconditioning cells to undergo cell death during the hypersensitive response as described by current models for systemic acquired resistance in dicot plants.

One candidate that may fit well in this role is salicylic acid (SA). SA, which exhibits a 10–50 fold increase during the HR and is also triggered in response to oxidative stresses associated with ozone or UV exposure (Hammond-Kosack and Jones (1996) Resistance Gene-dependent Plant Defense Responses, *Plant Cell* 8:1773–1791); Ryals et al. (1996) Systemic Acquired Resistance, *Plant Cell* 8:1809–1819), is known to cause $H_2O_2$ buildup (Chen et al. (1993) Involvement of Reactive Oxygen Species in the Induction of Systemic Acquired Resistance by Salicyclic Acid in Plants, *Science* 242:883–886) and transmute into a cell damaging free radical under oxidinzing conditions (Durner and Klessig (1996) Salicylic Acid is a Modulator of Tobacco and Mammalian Catalases, *J. Biol. Chem.*, 271:28492–28501). These attributes of SA indicate that it may be a mediator of cell death in lls1 mutants, a hypothesis fuly compatible with the demonstrated dependence on SA of cell death associated with a number of Arabidopsis lsd mutants (Dangl et al. (1996) Death Don't Have no Mercy. Cell Death Programs in Plant-microbe Interactions, *Plant Cell* 8:1793–1807; Weyman et al. (1996) Suppression and Restoration of Lesion Formation in Arabidopsis lsd mutants, *Plant Cell* 12:2013–2022). However, as noted above, the possibility nevertheless remains that a novel compound or mechanism is responsible for lls1-associated cell death.

The predicted association of LLS1 with an iron-sulfur cluster suggests that it may also participate in oxidation-reduction reactions. Proteins that use iron-sulfur clusters as prosthetic groups often function as biosensors of oxidants and iron (Roualt and Klausner (1996) Iron-sulfr Clusters as Biosensors of Oxidants and Iron, *Trends Biochem. Sci.* 21:174–177). LLS1 may also serve as a kind of rheostat such as that proposed for LSD1 in regulating cell death in plants (Jabs et al. (1996) Initiation of Runaway Cell Death in an Arabidopsis Mutant by Extracellular Superoxide, *Science* 273:1853–1856).

Working Model for lls1 Function

As noted earlier, the present invention is not dependent upon a particular mode of action. However, it is predicted that the LLS1 protein functions to inhibit the action of a cell "suicide factor" by degrading that factor. The suicide factor is a phenolic compound that is either a toxin or signal associated with photosynthetic stress or wounding or due to metabolic upset in the case of lls1/LeslO1 double mutants. Phenolics can cause superoxide production formation by donating an electron to dioxygen while in a semiquinone form (Appel (1993) Phenolics in Ecological Interactions: The Importance of Oxidation, *J. Chem. Ecol.* 19:1521–1552). Photosynthetic organisms have evolved multiple mechanisms to dissipate excess energy and avoid the production of reactive oxygen intermediates (ROI) during photosynthesis. Free-radicals are scavenged by ascorbate, carotenoids, the xanthophyll cycle, alpha-tocopherol, glutathione, and various phenolics (Alscher et al. (1993), *Antioxidants in Higher Plants*). The oxidative state of a cell influences dramatically the ability of phenolics to promote free radical formation (Appel (1993) Phenolics in Ecological Interactions: The Importance of Oxidation, *J. Chem. Ecol.* 19:1521–1552). The development of lls1 lesions could result in cell death due to the inability to remove a toxic phenolic or signal that has accumulated in a cell.

Whereas a toxin may directly inhibit basic metabolic processes a signal may trigger a programmed cell death pathway that is reminiscent of the hypersensitive response. Lesions thus spread because the release of the contents of dying cells cause oxidative stress in surrounding cells and result in the autocatalytic production of the cell suicide factor. Alternatively a signal for cell death may activate cell death programs in surrounding cells unless it is removed. The developmental gradient of lls1 lesion expression may reflect the accumulation of a suicide factor in older cells. Young tissue does not form lesions when wounded and this may reflect the lack of accumulation of a suicide factor, the inability to yet synthesize that compound or the existence of a juvenile lls1 homolog. Protection of the plant tissue from light would directly reduce the concentration of the suicide factor and avoid lesion formation. The concentric circle appearance of lls1 lesions may thus result from variation in the production of the suicide factor due to diurnal light cycles. Revertant sectors would be resistant to this suicide factor and the ability of lesions to "traverse" pale green or albino sectors in lls1/lls1 io/io or lls1/lls1 NCS7 double mutants would reflect the concentration and diffusibility of the toxic phenolics across tissues less able or unable to produce the suicide factor. In normal tissues functional LLS1 limits the effect of a suicide factor released in the process of wounding or stress. Finally it is expected that if LLS1 affects phenolic metabolism that a change in phenolic profile would occur in lls1 plants. Significantly, this prediction is supported by the report that a para-coumaric ester accumulates in lls1 lesioned plants but not in normal wild-type siblings or wild-type siblings inoculated with the fungus *Cochliobolus heterostrophus* (Obanni et al. (1994) Phenylpropanoid accumulation and Symptom Expression in the Lethal Leaf Spot Mutant of Maize, *Physiol. Mol. Plant Path.* 44:379–388).

lls1 May Play a Role in the Hypersensitive Response

A complex series of cellular events is envisaged to occur during the activation of defense responses in plants (Hammond-Kosact et al. (1996) Resistance Gene-dependent Plant Defense Responses, *Plant Cell* 8:1773–1791). Incompatible responses will often lead to the death of an infected cell within a few hours of infection. There is considerable evidence that this hypersensitive response (HR) is a form of programmed cell death activated by the plant cell. Lesion mimic mutations may cause an uncoupling of the regulatory steps of this process. Recent evidence has shown that control of cell death involves checkpoints that negatively and positively modulate the decision to progress to cell collapse. Evidence is provided by the observation that the lesion mimic phenotype of the lsd1 and lsd6 mutations of Arabidopsis are suppressed in the presence of the transgene nahG which degrades salicylic acid (SA). Application of 2,6 dichlorisonicotinic acid (a chemical inducer of systemic acquired resistance—SAR) restored lesion phenotype of these mutants (Dangl et al. (1996) *Plant Cell* 8:1793–1807). This result directly implicates SA in the signalling pathway that leads to cell death in these lesion mimics and that normally LSD1 and LSD6 would serve to negatively modulate that pathway. acd1 plants form spreading lesions in the presence of a functional lsd1 gene suggesting that ACD1 operates downstream or on a separate pathway from LSD1. Also there is evidence to indicate that SA donates an electron to catalase and in so doing becomes a free radical which interacts with membrane lipids to promote lipid peroxides which further promote membrane damage and cell collapse. Collectively these results suggest that acd1 functions downstream of lsd1 to inhibit a cell death pathway that is promoted by superoxide via SA and it may be that acd1 transcription is activated by LSD1. ACD1/LLS1 may degrade SA and thus negatively regulate a signalling pathway that could lead to runaway promotion of cell death. ACD1/LLS1 may be positively regulated by competing sensors of well being within the cell via the LSD1 protein and or other activators. Thus in an lls1 mutant what normally may constitute a minimal stress may become exaggerated through a runaway amplification loop and cell death pathways may be triggered resulting in lesion formation. This model predicts that nahG in an acd1/acd1 mutant will abolish lesion formation.

Cell Death Mechanisms in Plants Versus Animals

Lesion mimic genes are now providing insight into the kinds of genes involved in regulating cell death in plants. Three lesion mimic genes have now been cloned and do not have related counterparts in animal systems. This suggests that cell death is regulated in plants in a manner very different from models describing cell death regulation in animals although a role for ROI seems common to both systems. The recently cloned mlo locus from barley has been shown to encode a membrane protein and the lsd1 gene from Arabidopsis may encode a transcriptional activator. Both of these genes may normally serve to interpret external or internal stress signals and when mutated turn on or off other genes that cause cell death or cell survival respectively. The lls1 gene appears to be encode an enzyme involved in suppressing the spread of cell death through some aspect of phenolic metabolism. Phenolic production has long been associated with cell death in plants but little understood at the molecular level. Studies of the cloned lls1 gene may afford unexpected insights into this important aspect of plant physiology.

Expression Profile of Lethal Leaf Spot 1 (lls1)

In leaves 2 and 4 of 16-days-olds wild-type seedlings (Mo17, B73), the strongest expression of lls1 is seen in both upper and lower epidermis and its derivatives (such as silica cells), in sklerenchyma cells on either side of vascular bundles, and in protoxylem elements. A weaker, but clearly discernible expression signal is observed in bundle sheath, mesophyll cells and mid rib parenchyma. Expression is undetectable in metaxylem, phloem and companion cells.

In 7-day-old darkgrown wild-type seedlings (B73), lls1 expression can be detected at low levels in a uniform distribution throughout most leaf cells. Slightly elevated levels can be found in coleoptile and mid rib of the two oldest leaves.

In leaves of the dominant lesion mimic mutant Les 101, and in the lls1 mutant itself, expression of lls1 is essentially the same as in wild-type.

For in situ expression analysis of lls1, a 0.7 kb NotI-PstI fragment from the middle of the cDNA was used to make labeled sense and antisense riboprobes.

Clones comprising the genomic sequence and cDNA sequence described herein were deposited on Nov. 14, 1996 with the American Type Culture Collection, Rockville, Md., and given accession numbers ATCC 97791 and ATCC 97792.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

SEQUENCE LISTING (1) GENERAL INFORMATION:

(iii) NUMBER OF SEQUENCES: 65

(2) INFORMATION FOR SEQ ID NO:1:

(i) SEQUENCE CHARACTERISTICS:
      (A) LENGTH: 1855 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 15..1574

(xi) SEQUENCE DESCRIPTION: SEQ ID NO:1:

```
CGTGCGGGGA GAAT ATG CGC GCG ACA ATC CCA GCC CTG TCG CTC CTG GTG            50
          Met Arg Ala Thr Ile Pro Ala Leu Ser Leu Leu Val
            1               5                  10

ACG CCG CGG CTC CCC TCG CTC GCC GTG CCG CTG GCT GGA GGC CGC CTC            98
Thr Pro Arg Leu Pro Ser Leu Ala Val Pro Leu Ala Gly Gly Arg Leu
         15                  20                  25

CGC GAG GGC GGT CGT TCT CGG ACC CGC CTC CGC GTG GCG GCG CCG ACG           146
Arg Glu Gly Gly Arg Ser Arg Thr Arg Leu Arg Val Ala Ala Pro Thr
     30                  35                  40

TCC GTA CCA GGG GAA GCG GCG GAG CAG GCG GAG CCG AGC ACG TCG GCG           194
Ser Val Pro Gly Glu Ala Ala Glu Gln Ala Glu Pro Ser Thr Ser Ala
 45              50                  55                      60

CCC GAG TCC GGC GAG AAG TTC TCG TGG AGG GAT CAC TGG TAC CCG GTC           242
Pro Glu Ser Gly Glu Lys Phe Ser Trp Arg Asp His Trp Tyr Pro Val
                 65                  70                  75

TCC CTC GTC GAG GAC CTC GAC CCC AGC CGC CCC ACC CCG TTC CAG CTC           290
Ser Leu Val Glu Asp Leu Asp Pro Ser Arg Pro Thr Pro Phe Gln Leu
             80                  85                  90

CTC AAC CGC GAC CTC GTC ATC TGG AAG GAA CCC AAG TCC GGC GAG TGG           338
Leu Asn Arg Asp Leu Val Ile Trp Lys Glu Pro Lys Ser Gly Glu Trp
         95                 100                 105

GTC GCG CTC GAC GAC CGC TGC CCC CAC CGC CTT GCC CCG CTC TCG GAG           386
Val Ala Leu Asp Asp Arg Cys Pro His Arg Leu Ala Pro Leu Ser Glu
     110                 115                 120

GGC AGG ATC GAT GAG ACG GGG TGC TTG CAG TGC TCG TAT CAC GGA TGG           434
Gly Arg Ile Asp Glu Thr Gly Cys Leu Gln Cys Ser Tyr His Gly Trp
125                 130                 135                 140

TCA TTC GAT GGC TCC GGC GCC TGC ACC AAG ATC CCC CAG GCC ATG CCC           482
Ser Phe Asp Gly Ser Gly Ala Cys Thr Lys Ile Pro Gln Ala Met Pro
                145                 150                 155

GAG GGT CCT GAG GCC CGT GCG GTG CGG TCA CCG AAG GCG TGC GCG ATC           530
Glu Gly Pro Glu Ala Arg Ala Val Arg Ser Pro Lys Ala Cys Ala Ile
            160                 165                 170

AAG TTC CCC ACC CTC GTC TCC CAG GGG CTG CTC TTC GTG TGG CCC GAT           578
Lys Phe Pro Thr Leu Val Ser Gln Gly Leu Leu Phe Val Trp Pro Asp
        175                 180                 185

GAG AAT GGG TGG GAG AAA GCG GCC GCC ACC AAG CCT CCA ATG TTG CCG           626
Glu Asn Gly Trp Glu Lys Ala Ala Ala Thr Lys Pro Pro Met Leu Pro
    190                 195                 200

AAA GAA TTT GAG GAC CCG GCC TTC TCC ACG GTG ACA ATC CAG AGG GAC           674
Lys Glu Phe Glu Asp Pro Ala Phe Ser Thr Val Thr Ile Gln Arg Asp
205                 210                 215                 220

TTG TTC TAT GGT TAT GAT ACG TTG ATG GAG AAC GTC TCT GAT CCG TCC           722
Leu Phe Tyr Gly Tyr Asp Thr Leu Met Glu Asn Val Ser Asp Pro Ser
                225                 230                 235

CAT ATA GAA TTT GCT CAC CAC AAG GTT ACT GGA CGA AGA GAT AGA GCC           770
His Ile Glu Phe Ala His His Lys Val Thr Gly Arg Arg Asp Arg Ala
            240                 245                 250

AGG CCT TTG ACA TTC AGG ATG GAA TCA AGT GGT GCC TGG GGT TAC TCA           818
Arg Pro Leu Thr Phe Arg Met Glu Ser Ser Gly Ala Trp Gly Tyr Ser
        255                 260                 265

GGA GCA AAT TCT GGT AAT CCT CGC ATT ACT GCA ACT TTT GAG GCC CCT           866
Gly Ala Asn Ser Gly Asn Pro Arg Ile Thr Ala Thr Phe Glu Ala Pro
    270                 275                 280

TGT TAT GCA TTG AAC AAA ATA GAG ATA GAC ACA AAG TTA CCC ATT TTT           914
Cys Tyr Ala Leu Asn Lys Ile Glu Ile Asp Thr Lys Leu Pro Ile Phe
285                 290                 295                 300

GGC GAC CAG AAA TGG GTC ATA TGG ATT TGC TCT TTC AAC ATT CCA ATG           962
Gly Asp Gln Lys Trp Val Ile Trp Ile Cys Ser Phe Asn Ile Pro Met
                305                 310                 315
```

```
GCC CCA GGG AAG ACT CGT TCT ATT GTC TGT AGC GCT CGA AAC TTT TTC    1010
Ala Pro Gly Lys Thr Arg Ser Ile Val Cys Ser Ala Arg Asn Phe Phe
            320                 325                 330

CAG TTC ACA ATG CCA GGA AAA GCA TGG TGG CAG CTT GTT CCT CGA TGG    1058
Gln Phe Thr Met Pro Gly Lys Ala Trp Trp Gln Leu Val Pro Arg Trp
                335                 340                 345

TAT GAA CAT TGG ACT TCA AAT TTG GTC TAT GAT GGC GAT ATG ATC GTT    1106
Tyr Glu His Trp Thr Ser Asn Leu Val Tyr Asp Gly Asp Met Ile Val
        350                 355                 360

CTT CAA GGC CAG GAG AAG ATT TTC CTA GCT GCA ACC AAG GAG TCT TCT    1154
Leu Gln Gly Gln Glu Lys Ile Phe Leu Ala Ala Thr Lys Glu Ser Ser
365                 370                 375                 380

ACG GAT ATT AAT CAG CAG TAC ACA AAG ATC ACA TTC ACG CCC ACA CAA    1202
Thr Asp Ile Asn Gln Gln Tyr Thr Lys Ile Thr Phe Thr Pro Thr Gln
            385                 390                 395

GCT GAT CGA TTT GTT TTA GCA TTC CGC ACA TGG CTA AGG AAA TTT GGC    1250
Ala Asp Arg Phe Val Leu Ala Phe Arg Thr Trp Leu Arg Lys Phe Gly
                400                 405                 410

AAT AGC CAG CCG GAG TGG TTT GGA AAT CCT ACA CAA GAA GCA TTG CCT    1298
Asn Ser Gln Pro Glu Trp Phe Gly Asn Pro Thr Gln Glu Ala Leu Pro
        415                 420                 425

TCC ACC GTC CTT TCA AAG CGC GAG ATG CTA GAC AGA TAC GAG CAG CAC    1346
Ser Thr Val Leu Ser Lys Arg Glu Met Leu Asp Arg Tyr Glu Gln His
430                 435                 440

ACG TTG AAA TGC TCG TCC TGC AAA GGA GCA TAT AAT GCA TTC CAG AAT    1394
Thr Leu Lys Cys Ser Ser Cys Lys Gly Ala Tyr Asn Ala Phe Gln Asn
445                 450                 455                 460

CTG CAG AAG GTA TTC ATG GGA GCG ACA GTA GTT TGC TGT GCT GCC GCT    1442
Leu Gln Lys Val Phe Met Gly Ala Thr Val Val Cys Cys Ala Ala Ala
                465                 470                 475

GGT ATT CCT CCA GAT GTT CAG CTC AGG TTA TTG ATC GGT GCG GCT GCT    1490
Gly Ile Pro Pro Asp Val Gln Leu Arg Leu Leu Ile Gly Ala Ala Ala
        480                 485                 490

TTG GTC AGT GCC GCT GTA GCA TAC GCA TTC CAT GAG CTC CAG AAG AAT    1538
Leu Val Ser Ala Ala Val Ala Tyr Ala Phe His Glu Leu Gln Lys Asn
            495                 500                 505

TTT GTA TTC GTG GAT TAC GTG CAT GCT GAC ATT GAT TGAAAGATTC         1584
Phe Val Phe Val Asp Tyr Val His Ala Asp Ile Asp
        510                 515                 520

GTGAGGATCT GTTGTGCGAC ATCACTGGCT CGCGAGTCGT GTCTGTAGTC TAGGGCTCTA  1644

GGCGTCTAGC TAGGGAAAGT AACTTTTTGC CGGGTATAGG TCATATTGCT CACATATGTA  1704

TTTTGTATAG TGTATGCACT CAACTGTAGC CGATTCAGTG CGAAAATATA GTTTTTATGT  1764

TACTATCTAT TGGATTAAAA TTGTCTCCAG ATCCTTTTAG CATGTAAAAT GCCATTTTTC  1824

AAATGGAAGT TCTCAATTGC GCCCCTAGAC T                                1855

(2) INFORMATION FOR SEQ ID NO:2:

(i) SEQUENCE CHARACTERISTICS:
        (A) LENGTH: 520 amino acids
        (B) TYPE: amino acid
        (D) TOPOLOGY: linear (ii) MOLECULE TYPE: protein (xi) SEQUENCE DESCRIPTION: SEQ ID NO:2:

Met Arg Ala Thr Ile Pro Ala Leu Ser Leu Leu Val Thr Pro Arg Leu
 1               5                  10                  15

Pro Ser Leu Ala Val Pro Leu Ala Gly Gly Arg Leu Arg Glu Gly Gly
```

-continued

```
             20                  25                  30
Arg Ser Arg Thr Arg Leu Arg Val Ala Ala Pro Thr Ser Val Pro Gly
         35                  40                  45
Glu Ala Ala Glu Gln Ala Glu Pro Ser Thr Ser Ala Pro Glu Ser Gly
 50                  55                  60
Glu Lys Phe Ser Trp Arg Asp His Trp Tyr Pro Val Ser Leu Val Glu
 65                  70                  75                  80
Asp Leu Asp Pro Ser Arg Pro Thr Pro Phe Gln Leu Leu Asn Arg Asp
                 85                  90                  95
Leu Val Ile Trp Lys Glu Pro Lys Ser Gly Glu Trp Val Ala Leu Asp
                100                 105                 110
Asp Arg Cys Pro His Arg Leu Ala Pro Leu Ser Glu Gly Arg Ile Asp
                115                 120                 125
Glu Thr Gly Cys Leu Gln Cys Ser Tyr His Gly Trp Ser Phe Asp Gly
                130                 135                 140
Ser Gly Ala Cys Thr Lys Ile Pro Gln Ala Met Pro Glu Gly Pro Glu
145                 150                 155                 160
Ala Arg Ala Val Arg Ser Pro Lys Ala Cys Ala Ile Lys Phe Pro Thr
                165                 170                 175
Leu Val Ser Gln Gly Leu Leu Phe Val Trp Pro Asp Glu Asn Gly Trp
                180                 185                 190
Glu Lys Ala Ala Ala Thr Lys Pro Pro Met Leu Pro Lys Glu Phe Glu
                195                 200                 205
Asp Pro Ala Phe Ser Thr Val Thr Ile Gln Arg Asp Leu Phe Tyr Gly
                210                 215                 220
Tyr Asp Thr Leu Met Glu Asn Val Ser Asp Pro Ser His Ile Glu Phe
225                 230                 235                 240
Ala His His Lys Val Thr Gly Arg Arg Asp Arg Ala Arg Pro Leu Thr
                245                 250                 255
Phe Arg Met Glu Ser Ser Gly Ala Trp Gly Tyr Ser Gly Ala Asn Ser
                260                 265                 270
Gly Asn Pro Arg Ile Thr Ala Thr Phe Glu Ala Pro Cys Tyr Ala Leu
                275                 280                 285
Asn Lys Ile Glu Ile Asp Thr Lys Leu Pro Ile Phe Gly Asp Gln Lys
                290                 295                 300
Trp Val Ile Trp Ile Cys Ser Phe Asn Ile Pro Met Ala Pro Gly Lys
305                 310                 315                 320
Thr Arg Ser Ile Val Cys Ser Ala Arg Asn Phe Gln Phe Thr Met
                325                 330                 335
Pro Gly Lys Ala Trp Trp Gln Leu Val Pro Arg Trp Tyr Glu His Trp
                340                 345                 350
Thr Ser Asn Leu Val Tyr Asp Gly Asp Met Ile Val Leu Gln Gly Gln
                355                 360                 365
Glu Lys Ile Phe Leu Ala Ala Thr Lys Glu Ser Ser Thr Asp Ile Asn
                370                 375                 380
Gln Gln Tyr Thr Lys Ile Thr Phe Thr Pro Thr Gln Ala Asp Arg Phe
385                 390                 395                 400
Val Leu Ala Phe Arg Thr Trp Leu Arg Lys Phe Gly Asn Ser Gln Pro
                405                 410                 415
Glu Trp Phe Gly Asn Pro Thr Gln Glu Ala Leu Pro Ser Thr Val Leu
                420                 425                 430
Ser Lys Arg Glu Met Leu Asp Arg Tyr Glu Gln His Thr Leu Lys Cys
                435                 440                 445
```

```
Ser Ser Cys Lys Gly Ala Tyr Asn Ala Phe Gln Asn Leu Gln Lys Val
    450                 455                 460

Phe Met Gly Ala Thr Val Val Cys Cys Ala Ala Ala Gly Ile Pro Pro
465                 470                 475                 480

Asp Val Gln Leu Arg Leu Leu Ile Gly Ala Ala Ala Leu Val Ser Ala
                485                 490                 495

Ala Val Ala Tyr Ala Phe His Glu Leu Gln Lys Asn Phe Val Phe Val
            500                 505                 510

Asp Tyr Val His Ala Asp Ile Asp
        515                 520

(2) INFORMATION FOR SEQ ID NO:3:

(i) SEQUENCE CHARACTERISTICS:
        (A) LENGTH: 2822 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:3:

GCAACGCACA CAGACAGGCA GCGATGTCTT TCGCGGGTCA GTAAACCTCA CTCACACAGG      60

CTATTCGTCT TAAGTTTTTT TGTTCAACAT CACATACTTG TGTTGCTAAT GTAACAAAAA     120

AAATTCACAC GCCTCACAAA CATTACAATA TGATTCAAAA TAGACACTAA CCAAACCTTG     180

GAGGACTTTG TACTGGCTAG AGAACACCTA CTCTACTGCT ATGCTGCTTA CCCGAGACAG     240

AGGAAATACA CACGAGCAAC TGTTGTGGAC TTGTTGCAAA ATAGCAAGGA AAGGTATTAG     300

TAATAGCAAG CATAATTGTA GGAGCTGCAA GTATAACAAT GATAGTCTGC TCTTTAGTAC     360

CTTACATGTA TGAAATAAAA AACTATATAG GTAAAGTGAA CAACATGCGT TATGTAAATC     420

TAGCAGACTA TTGGATTGAA AAGAATTCAA TTACAAGGAC AAAGAATGAC TGACGAGGGC     480

AGCAACACAA TAACTAAATG TTCCAAAATG GTCAGATATG AAGGGCTCGA ACGCATGCAC     540

GGCATGATAT GCTAGTTGGG GCCGTTTCCG TCGGGCTTTA AGATAAGGA AATCTGGATA      600

TGGACTAATG ATGTCTAATT TTTGTTAGAG CCTAGCGCCC TAGCATGCTA ACTAGAAGGT     660

TAATTTTGTT TCTATTTTTT GTTGCACCGA CTGAGCCAAC ATTCTTTTGT CTAGTAGTTT     720

ACATTTTAGT TACTACTCTC TTCGTCTAAA AAGTACTATA TCTCCATTTT TTAAAATGTC     780

TTGCTTTTTG AAGAGCACTA TCTTTTAAAA TCTTGACCAA CTATATAAAA GTACTTCTGA     840

TACATGATAG GTTAATAAA ATATATAAAA TCTTATATTT TTAGTAAGTC TAGTCAAACT      900

TAAGAGCTTT TGATGTCGCA CATAGTTGTT TTAAACAAGG TGTTTGTTCA TGTTCGTTCT     960

AATATGTGGA TAGTATTCCG ATTCATTTCG CCAGAGGTGT GGCTGTGGAT ATTTGGTTAG    1020

AGCATCTTCA AGAAAACCCG TAAATCAACT CCAAAAACGT TTTGAGCCTC CAACAGTCC     1080

CCCTTCCCCT CCCCATATTA CGCGTCAAGC ATTGTTCCCA ATCGTCCTCT GCGCATGCTG    1140

GTTCCCACGT GTATTTTCCT CGCGCGCAGT TCTGTTGGAG GAGGAAGGCG GGACGTTGGC    1200

ACTAGCGCTG GCTGGAGATT ATGGCCATCG CAATCAGTTT GTGGCAGTCA AATGCTTTGT    1260

TTTTTTGGCC GCTCATGTGA GTATCATTTC TGTGAAAACT ATCTAAATCA ATATGAATGT    1320

ATATTTCTTT AAGTCGTCAC GATAGGAAGA CTCCATCGTT CTAAAACCTA AACCATGCAC    1380

ACATATTCAT CTTTCTCCAA ACGCAAGTCT CGTGATATTT ATATTCTCGT GCCAGCTAGA    1440

TTATCTAGAA ATTTAGATTC TTAAAAAAAT TCTTTAGAAA AAAAATTATA CCAAACAGGA    1500
```

-continued

```
CCATGGTTTA AACTATTACG GATAAATAGC ATGACTACCT TAGTATTTAA ATGATATCAG     1560

TTGAAATATG TCGACTTATT TTATAGTTAG TATTATTAGA ACATGTTTAA ATAATTATCA     1620

CATTTAAACC AGATCTACAT ATAAACTATT TTGCTTGTCA ACTGCATCGC AAACTCACTT     1680

GCCTACCATC GGGATCGCGC TCGTATACAA GTGACACACT TTAAATGATT TAAGCCGCGA     1740

AAATTATAAA TGTACCATCC TCATTTGGCA AGTCTAAAGA TAGCTTTACC ATACAAATGA     1800

AACTAAATTT AAAATTCCAA GTAATAATTA GAAAAACTGA TTTGACAGTT TTTTCAGTAT     1860

ATATTTAGCA GCTCGCTAAA TCTGAATTTA GAAAGTTTTT TTGAAATGAG TTGAGATGCT     1920

CTTATAATGG TTACTATAGG TTGAGGGACG GAAGTAGTAG TAGAACTGGT AAACAAATTC     1980

GAATTTGATC TATTCAACTT TGTAGCTACT CAGCAAGATG CGAATTGCAA ACATCCGGCG     2040

GGGTGGATTC CGCCACGGCC CACGGGTGGG TTCGTGTCGT TCTCACCGCC GGTCAATCTC     2100

CCCTCCGCGC GGCGCAATTC GTCCCGGTGG GGACGGCTAG CTGGCCCAAT GCCAAAGCTC     2160

CACCGACAAA TGCCGCAAAG CGCCATGCGT GGTCGCGTAC AATTGCCTCC TTCCCCGCCC     2220

TTCCTCCCTT CCCTGCCGTG ACGCAACCAC ACTGCGCTCA CCATCGTGTA CAATGTATTC     2280

TCCCTAGCCG AACCGTATCA GTAGTTCTTA GGGGTGGGCG TTCGGGTTAC CCGAAATTTT     2340

CGGGTTGGGT AATTCAAGTT TTTTAAATTT CGGGTTTTGA GAATCAATAC CCGAAATTAC     2400

AACGGATTTT TCAATACCCG GAATTTCGGG TACCCGGAAT TTCGGGTTCG GGTTCGGGTA     2460

TTCCCAAACT ACCCGAACTA TTGTGTTGGC TTCATAAAAA CACATACACC CTATTAAATT     2520

AGTATAAAAA TATAGTTTGA ATAATGATAT ACATGGACAT ATAAAACACA AACAATCTAC     2580

AATCCCAAGT TATGCACACT TACACATAAT TATAGATGTA CAAACTTAAA TTATTAAAGC     2640

ATGACATGAG TACATGACAC ATGAAAGCCG GGTAATTCGG GTATTTCGGG TACCCGATTG     2700

TGATACCCGA ATTACCCGAA ATAATTTCGG GTTTTGCAAG TTGCTACCCG AAATTCCCAA     2760

ACAAAATTCG GGTTTCGGGT ATTTCGGGTT CGGGTTCGGG TATTCCAGGT TTGGGTTTCG     2820

GG                                                                    2822
```

(2) INFORMATION FOR SEQ ID NO:4:

(i) SEQUENCE CHARACTERISTICS:
        (A) LENGTH: 4015 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:4:

```
TTACGGGTTT TTTGCCCAGC CCTACTAGTT CTTCCCTCGC GTTCACTCCC CAGCGTGGGA       60

AAATCCCGGA ATTTTCTTGT TTGTCCACTG GTTTTCTTGC GCCAAAACCA GGTTTCTCCC      120

CGTTGCCGTG GCAGAACTCT GTTCTTGCCC AGTCTAGAAG ATCTGCACCG TTCCAACCAC      180

CGACTCCGGC CGCCAAGCAT ATAGCCAGCG CGGCGAAGAA TTCCCAACGC GAAAGCCAAA      240

ACCTCTTCAC TTCACTTCAC GTCGACACGT GCGGGGAGAA TATGCGCGCG ACAATCCCAG      300

CCCTGTCGCT CCTGGTGACG CCGCGGCTCC CCTCGCTCGC CGTGCCGCTG GCTGGAGGCC      360

GCCTCCGCGA GGGCGGTCGT TCTCGGACCC GCCTCCGCGT GGCGGCGCCG ACGTCCGTAC      420

CAGGGGAAGC GGCGGAGCAG GCGGAGCCGA GCACGTCGGC GCCCGAGTCC GGCGAGAAGT      480

TCTCGTGGAG GGATCACTGG TACCCGGTCT CCCTCGTCGA GGACCTCGAC CCCAGCCGCC      540

CCACCCCGTT CCAGCTCCTC AACCGCGACC TCGTCATCTG GAAGGAACCC AAGTCCGGCG      600
```

```
AGTGGGTCGC GCTCGACGAC CGCTGCCCCC ACCGCCTTGC CCCGCTCTCG GTACGGCGAC    660

CCGCATCCCT TCCTCGCCTC ATCCGTGTCC TACCGGATCT CTTCCTCGTT TCGGCTAATT    720

TTGGTCTGGG CATGTGCAGG AGGGCAGGAT CGATGAGACG GGGTGCTTGC AGTGCTCGTA    780

TCACGGATGG TCATTCGATG GCTCCGGCGC CTGCACCAAG ATCCCCCAGG CCATGCCCGA    840

GGGTCCTGAG GCCCGWGCGG TGCGGTCACC GAAGGCGTGC GCGATCAAGT TCCCCACCCT    900

CGTCTCCCAG GGGCTGCTCT TCGTGTGGCC CGATGAGAAT GGGTGGGAGA AGCGGCCGC     960

CACCAAGCCT CCAATGTGCG TAGAGTCAGA CTTTGGACTG CGGCTAATTG GTTGGATTCA    1020

GTTTTGCATT TCGGTGTCTG AATTCGATCT TATTTGGTTT CAGGTTGCCG AAAGAATTTG    1080

AGGACCCGGC CTTCTCCACG GTGACAATCC AGAGGGACTT GTTCTATGGT TATGATACGT    1140

TGATGGAGAA CGTCTCTGAT CCGTCCCATA TAGAATTTGC TCACCACAAG GTACTTGGTA    1200

CAGTGAGAAA GCTTAGTTGC TTGCCACACT TAAGCACCAT GATAGTATTT TTCAGTTGAA    1260

AGTTGGTGAT TCGAGGAAAG ATGTTTTGTT GCAACCAATT TGTGTAGTTT GCTAAAAAAT    1320

CACCTCCTCA ATACTGTTTA ATTGTGTAGG CCTCTTATCG TTTCTGATTG CCAGTGTGCA    1380

AGTTTAACTA ACTGTTAGAT CTTAACTGTG GATGTACCCA TATATTTTTT TTGCATCATA    1440

GTTTTATTCT TTTTTACTTA TGCTGCATTG AAATTCCTCA GAAATGACTT ATAATGGGCA    1500

AAAGGGCTGA ATGGCTGAGT CTGGCCTCTT ATCGTTTCTA GATTGCCAGC GTGCAAGTTT    1560

AACTAAGGTC CCGTTTGGTT TGAGGGATTA AATATCAGTG CCTCCATTTT AGTCCCATTT    1620

AGTCCATAAA TTGACAAACG GTGGGACTAA ACAAGGACT AAACTGTTCT AGTCTCTAGT    1680

CCCTCAAGGG ATGACTCTAA GGGGCTAAAC CATAAAAATC CACTTTTTGG CCCTCCTTCA    1740

TTTCAGTTGC ACTAATGGCG GGAGGATGTT AAGGAGTATT TTGGTCTTCT TATGATTCAT    1800

TTAATGTGTT TTGAATACTT ATAGTTTTTA GAACCAAACA GGGAGGGACT AAATTTTAGT    1860

CTTCTAACTA AACTTTCGTC CCTGGACTAA AGGAACCAAA CCCTAACTGT TAGATCTTAA    1920

CTGTGGATGC ACCCATATAT ATTTTTGCAT CATAGTTTTA GTTCTTTTTT ACTTACGCTA    1980

CTTGCTTAGT CTGAACAGGC ATTAATAGGG TGTTTGGTTT GAGGGATTAG TTAGTTCACC    2040

CACTCATTCC TCTTTTCTTT GTTTGGTTTG TTGAATGGAG TAGGTTGGTC AGTGCATTAT    2100

CACATCATTC CTCAGACTAG TAGTTAGTAC TAGTATGAAG AATGGGGTCA TTCAACCAAA    2160

TTTAAGGAAT TGACTCATGA TGCATCACCA CATTTAGAAT GGAGTGGCTC CTCAAACCAA    2220

ACCCTATAAA TGACTGGCTG AGTTAATTGT GCTATCTGTG TGTCATGAAC TTGTGCCGGC    2280

AGCATAGACA AACAAAATGC TTTATTTTCT CGGGATACAT GGTTTCAGCA AATCCACTCA    2340

TGTTTCAGAT TTTAACTCTT CACAGGTTAC TGGACGAAGA GATAGAGCCA GGCCTTTGAC    2400

ATTCAGGATG GAATCAAGTG GTGCCTGGGG TTACTCAGGA GCAAATTCTG GTAATCCTCG    2460

CATTACTGCA ACTTTTGAGG CCCCTTGTTA TGCATTAAAC AAGTAAGTTT CAGAAAAGTA    2520

CCTGGTCATC TTTGAGTGTG GAGTGATTCT TATTTACCAC TTAAGCAATT CAGTCGTTAT    2580

ACGGTTCTGA ACTTCTGTTA ACTGGCTTGT ACAGAATAGA GATAGACACA AAGTTACCCA    2640

TTTTTGGCGA CCAGAAATGG GTCATATGGA TTTGCTCTTT CAACATTCCA ATGGCCCCAG    2700

GGAAGACTCG TTCTATTGTC TGTAGCGCTC GAAACTTTTT CCAGTTCACA ATGCCAGGAA    2760

AAGCATGGTG GCAGGTACAT GTGTGTTTAG TGTTTCCTTT ACTTAAGCTT TGTTTTCCTA    2820

TTTGTTTTGT CAACATAATC TTTTAACTGC TAAAACGAAC TTGTTCTCGC GTTTTTGTGG    2880

GAAACAAGGC AAAGGTCCCT AGTCCCTACT GTAGGCATAT ATTATTGGCA GAGTTTATTA    2940

CTTGGTCATG TTTGAATTTA TATGTGTACA GTCAAATGTT GATAGCTTCT TTCTCTTGGT    3000
```

```
GTAGCTTGTT CCTCGATGGT ATGAACATTG GACTTCAAAT TTGGTCTATG ATGGCGATAT    3060

GATCGTTCTT CAAGGCCAGG AGAAGATTTT CCTAGCTGCA ACCAAGGAGT CTTCTACGGA    3120

TATTAATCAG CAGTACACAA AGATCACATT CACGCCCACA CAAGCTGATC GATTTGTTTT    3180

AGCATGCCGC ACGTGGCTAA GGAAATTTGG CAATAGCCAG CCGGAGTGGT TTGGAAATCC    3240

TACACAAGAA GCATTGCCTT CCACCGTCCT TTCAAAGCGC GAGGTAAAAG CCATCTGGGT    3300

CACCAAAAAA GTTTCAGTAT AATATTTGCT TCAGACATAA AATATCTGAA TATGACAACC    3360

TTTTTGGTGG TCAAAGATCT GTTTTGCTTA CATTCTTAAT ACTCGATGCA TTGGTAAGTT    3420

ATTACAGTTA TCCTTTTTAC TCGATTTTTC CCTTTCTGAG CAGAACTATT ATCACGTCTT    3480

CATTGTTTGT ACACTTGGTT TCTATGACAC ACAAATTTTT ATTTTACATT ATCAGTTGTC    3540

ATATGAACTA ATGTATTTAC AGCAACCTGC TTAAGTGCTT AGTATCACAA AGGGACAAAT    3600

TCAATGAAAT ATTTGGAAAG ATAGTAGCGT CGAACCACTC TCACAGCTAG CATTTGAGA     3660

ATAGTTACTT AACTGACAGC GAAGTTCACC TTCTACCGAC TGGATCTGGA AACAGTATCT    3720

TGAAGTAGTT CACACGTAAA CCTTCATCAG CTGTGTTTCT GGCTTCCAGT AACTCATGTA    3780

TTCTTATGAT TGACTTTGTG TTATGCAGAT GCTAGACAGA TACGAGCAGC TCTCGTTGAA    3840

ATGCTCGTCT TGCAAAGGAG CATATAATGC TTTCCAGAAT CTGCAGAAGG TATTCATGGG    3900

AGCGACAGTA GTTTGCTGTG CTGCCGCTGG TATTCCTCCA GATGTTCAGC TCAGGCTATT    3960

GATCGGTGCG GCTGCTTTGG TCAGTGCCGC TATAGCATAC GCATTCCATG AGCTC         4015
```

(2) INFORMATION FOR SEQ ID NO:5:

(i) SEQUENCE CHARACTERISTICS:
        (A) LENGTH: 520 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:5:

```
Pro Ile Gln Lys Asp Ser Leu Phe Ile Ser His His Lys Ile Pro Ile
1               5                  10                  15

Lys Gly Leu Asn Phe Ser Ile Lys Ile Glu Thr Phe Pro Gln Pro Phe
            20                  25                  30

Thr Arg Gly Gly Ala Ala Val Leu Tyr Pro Leu Arg Ile Arg Arg Arg
        35                  40                  45

Arg Ser Gly Ser Lys Lys Asn Thr Gly Gly Asp Lys Glu Glu Glu Gly
    50                  55                  60

Ser Glu Phe Lys Trp Arg Asp His Trp Tyr Pro Val Ser Leu Val Glu
65                  70                  75                  80

Asp Leu Val Pro Asn Val Pro Thr Pro Phe Gln Leu Leu Gly Arg Asp
                85                  90                  95

Leu Val Leu Trp Phe Asp Arg Asn Asp Gln Lys Trp Ala Ala Leu Phe
            100                 105                 110

Tyr Gly Tyr Asp Thr Leu Met Glu Asn Val Ser Asp Pro Ser His Ile
        115                 120                 125

Asp Phe Ala His His Lys Val Thr Gly Arg Arg Asp Arg Ala Lys Pro
    130                 135                 140

Leu Pro Phe Lys Val Glu Ser Ser Gly Pro Trp Gly Phe Gln Gly Ala
145                 150                 155                 160

Asn Asp Asp Ser Pro Arg Ile Thr Ala Lys Val Ala Pro Cys Tyr Ser
```

-continued

```
                165                 170                 175
Met Asn Lys Ile Glu Leu Asp Ala Lys Leu Pro Ile Val Gly Asn Gln
            180                 185                 190

Lys Trp Val Ile Trp Ile Cys Ser Phe Asn Ile Pro Met Ala Pro Gly
        195                 200                 205

Lys Thr Arg Ser Ile Val Cys Ser Ala Arg Asn Phe Asp Asp Leu Cys
    210                 215                 220

Pro His Arg Leu Ala Pro Leu Ser Glu Gly Arg Leu Asp Glu Asn Gly
225                 230                 235                 240

His Leu Gln Cys Ser Tyr His Gly Trp Ser Phe Gly Cys Gly Ser
                245                 250                 255

Cys Thr Arg Ile Pro Gln Ala Ala Thr Ser Gly Pro Glu Ala Arg Ala
            260                 265                 270

Val Lys Ser Pro Arg Ala Cys Ala Ile Lys Phe Pro Thr Met Val Ser
        275                 280                 285

Gln Gly Leu Leu Phe Val Trp Pro Asp Glu Asn Gly Trp Asp Arg Ala
    290                 295                 300

Asn Ser Ile Glu Pro Pro Arg Leu Pro Asp Asp Phe Asp Lys Pro Glu
305                 310                 315                 320

Phe Ser Thr Val Thr Ile Gln Arg Asp Phe Gln Phe Ser Val Pro
                325                 330                 335

Gly Pro Ala Trp Trp Gln Val Pro Arg Trp Tyr Glu His Trp Thr Ser
            340                 345                 350

Asn Leu Val Tyr Asp Gly Asp Met Ile Val Leu Gln Gly Gln Glu Lys
        355                 360                 365

Val Phe Leu Ala Lys Ser Met Glu Ser Pro Asp Tyr Asp Val Asn Lys
    370                 375                 380

Gln Tyr Thr Lys Leu Thr Phe Thr Pro Thr Gln Ala Asp Arg Phe Val
385                 390                 395                 400

Leu Ala Phe Arg Asn Trp Leu Arg Arg His Gly Lys Ser Gln Pro Glu
                405                 410                 415

Trp Phe Gly Ser Thr Pro Ser Asn Gln Pro Leu Pro Ser Thr Val Leu
            420                 425                 430

Thr Lys Arg Gln Met Leu Asp Arg Phe Asp Gln His Thr Gln Val Cys
        435                 440                 445

Ser Ser Cys Lys Gly Ala Tyr Asn Ser Phe Gln Ile Leu Lys Lys Phe
    450                 455                 460

Leu Val Gly Ala Thr Val Phe Trp Ala Ala Thr Ala Gly Val Pro Ser
465                 470                 475                 480

Asp Val Gln Ile Arg Leu Val Leu Ala Gly Leu Ser Leu Ile Ser Ala
                485                 490                 495

Ala Ser Ala Tyr Ala Leu His Glu Gln Glu Lys Asn Phe Val Phe Arg
            500                 505                 510

Asp Tyr Val His Ser Glu Ile Glu
        515                 520
```

(2) INFORMATION FOR SEQ ID NO:6:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:6:

Cys Xaa His Xaa Cys Xaa His
1               5

(2) INFORMATION FOR SEQ ID NO:7:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:7:

Glu Xaa Asp Xaa His Xaa His
1               5

(2) INFORMATION FOR SEQ ID NO:8:

(i) SEQUENCE CHARACTERISTICS:
        (A) LENGTH: 35 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:8:

Asn Gln Cys His His Arg Gly Met Lys Leu Ser Arg Asp Asp Ala Gly
1               5                   10                  15

Asn Ala Lys Ala Pro Val Cys Thr Tyr His Gly Trp Ala His Asp Ile
            20                  25                  30

Ser Gly Gln
        35

(2) INFORMATION FOR SEQ ID NO:9:

(i) SEQUENCE CHARACTERISTICS:
        (A) LENGTH: 35 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:9:

Asn Gln Cys Arg His Arg Gly Met Arg Ile Cys Arg Ser Asp Ala Gly
1               5                   10                  15

Asn Ala Lys Ala Pro Thr Cys Ser Tyr His Gly Trp Ala Tyr Asp Ile
            20                  25                  30

Ala Gly Lys
        35

(2) INFORMATION FOR SEQ ID NO:10:

(i) SEQUENCE CHARACTERISTICS:
        (A) LENGTH: 35 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:10:

Asn Gln Cys Arg His Arg Gly Met Arg Ile Cys Arg Ser Asp Ala Gly

```
1               5              10              15
Asn Ala Lys Ala Pro Thr Cys Thr Tyr His Gly Trp Ala Tyr Asp Ile
            20              25              30
Ala Gly Asn
        35
```

(2) INFORMATION FOR SEQ ID NO:11:

(i) SEQUENCE CHARACTERISTICS:
        (A) LENGTH: 35 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:11:

```
Asn Gln Cys Arg His Arg Gly Met Arg Ile Val Arg Ser Asp Gly Gly
1               5              10              15
Asn Ala Lys Ala Pro Thr Cys Thr Tyr His Gly Trp Ala Tyr Asp Ile
            20              25              30
Ala Gly Asn
        35
```

(2) INFORMATION FOR SEQ ID NO:12:

(i) SEQUENCE CHARACTERISTICS:
        (A) LENGTH: 35 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:12:

```
Asn Gln Cys Arg His Arg Gly Met Arg Ile Cys Arg Ala Asp Ala Gly
1               5              10              15
Asn Ala Lys Ala Pro Thr Cys Ser Tyr His Gly Trp Ala Tyr Asp Thr
            20              25              30
Ala Gly Asn
        35
```

(2) INFORMATION FOR SEQ ID NO:13:

(i) SEQUENCE CHARACTERISTICS:
        (A) LENGTH: 35 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:13:

```
Asn Gln Cys Arg His Arg Gly Met Arg Ile Cys Arg Ser Asp Ala Gly
1               5              10              15
Asn Ala Lys Ala Pro Thr Cys Ser Tyr His Gly Trp Ala Tyr Asp Thr
            20              25              30
Ala Gly Asn
        35
```

(2) INFORMATION FOR SEQ ID NO:14:

(i) SEQUENCE CHARACTERISTICS:
        (A) LENGTH: 35 amino acids (B) TYPE: amino acid
            (C) STRANDEDNESS:
            (D) TOPOLOGY: linear (ii) MOLECULE TYPE: protein (xi) SEQUENCE DESCRIPTION: SEQ ID NO:14:

Asn Gln Cys Arg His Arg Gly Met Arg Ile Cys Arg Ala Asp Gly Gly
1               5                   10                  15

Asn Ala Lys Ser Pro Thr Cys Ser Tyr His Gly Trp Ala Tyr Asp Ser
            20                  25                  30

Ala Gly Asn
        35

(2) INFORMATION FOR SEQ ID NO:15:

(i) SEQUENCE CHARACTERISTICS:
            (A) LENGTH: 35 amino acids
            (B) TYPE: amino acid
            (C) STRANDEDNESS:
            (D) TOPOLOGY: linear (ii) MOLECULE TYPE: protein (xi) SEQUENCE DESCRIPTION: SEQ ID NO:15:

Asn Gln Cys Arg His Arg Gly Met Arg Ile Cys Arg Ala Asp Gly Gly
1               5                   10                  15

Asn Ala Lys Ser Pro Thr Cys Ser Tyr His Gly Trp Ala Tyr Asp Thr
            20                  25                  30

Gly Gly Asn
        35

(2) INFORMATION FOR SEQ ID NO:16:

(i) SEQUENCE CHARACTERISTICS:
            (A) LENGTH: 35 amino acids
            (B) TYPE: amino acid
            (C) STRANDEDNESS:
            (D) TOPOLOGY: linear (ii) MOLECULE TYPE: protein (xi) SEQUENCE DESCRIPTION: SEQ ID NO:16:

Asn Ala Cys Ser His Arg Gly Ala Gln Leu Leu Gly His Lys Arg Gly
1               5                   10                  15

Asn Lys Thr Thr Tyr Thr Cys Pro Phe His Gly Trp Thr Phe Asn Asn
            20                  25                  30

Ser Gly Lys
        35

(2) INFORMATION FOR SEQ ID NO:17:

(i) SEQUENCE CHARACTERISTICS:
            (A) LENGTH: 35 amino acids
            (B) TYPE: amino acid
            (C) STRANDEDNESS:
            (D) TOPOLOGY: linear (ii) MOLECULE TYPE: protein (xi) SEQUENCE DESCRIPTION: SEQ ID NO:17:

Asn Ala Cys Ser His Arg Gly Ala Thr Leu Cys Arg Phe Arg Ser Gly
1               5                   10                  15

Asn Lys Ala Thr His Thr Cys Ser Phe His Gly Trp Thr Phe Ser Asn
            20                  25                  30

```
Ser Gly Lys
        35

(2) INFORMATION FOR SEQ ID NO:18:

(i) SEQUENCE CHARACTERISTICS:
        (A) LENGTH: 35 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:18:

Asn Ser Cys Arg His Arg Gly Ala Leu Leu Cys Pro Phe Ser Lys Gly
1               5                   10                  15

Asn Gln Lys Phe His Val Cys Arg Tyr His Gly Trp Ser Tyr Asp Ser
            20                  25                  30

Ser Gly Arg
        35

(2) INFORMATION FOR SEQ ID NO:19:

(i) SEQUENCE CHARACTERISTICS:
        (A) LENGTH: 35 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:19:

Asn Val Cys Arg His Arg Gly Lys Thr Leu Val Ser Val Glu Ala Gly
1               5                   10                  15

Asn Ala Lys Gly Pro Val Cys Ser Tyr His Gly Trp Gly Phe Gly Ser
            20                  25                  30

Asn Gly Lys
        35

(2) INFORMATION FOR SEQ ID NO:20:

(i) SEQUENCE CHARACTERISTICS:
        (A) LENGTH: 35 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:20:

Asn Val Cys Arg His Arg Gly Lys Thr Leu Val Asn Ala Glu Ala Gly
1               5                   10                  15

Asn Ala Lys Gly Pro Val Cys Gly Tyr His Gly Trp Gly Phe Gly Ser
            20                  25                  30

Asn Gly Lys
        35

(2) INFORMATION FOR SEQ ID NO:21:

(i) SEQUENCE CHARACTERISTICS:
        (A) LENGTH: 35 amino acids
        (B) TYPE: amino acid
        (C) STRANDEDNESS:
        (D) TOPOLOGY: linear
```

(ii) MOLECULE TYPE: protein (xi) SEQUENCE DESCRIPTION: SEQ ID NO:21:

Asn Val Cys Arg His Arg Gly Lys Thr Ile Val Asp Ala Glu Ala Gly
1               5                   10                  15
Asn Ala Lys Gly Pro Val Cys Gly Tyr His Gly Trp Gly Tyr Gly Ser
            20                  25                  30
Asn Gly Lys
        35

(2) INFORMATION FOR SEQ ID NO:22:

(i) SEQUENCE CHARACTERISTICS:
        (A) LENGTH: 34 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:22:

Ser Arg Cys Pro His Arg Gly Val Ser Leu Phe Met Gly Arg Val Lys
1               5                   10                  15
Lys Gly Gly Leu Arg Cys Val Tyr His Gly Trp Lys Phe Ser Ala Glu
            20                  25                  30
Gly Lys (2) INFORMATION FOR SEQ ID NO:23:

(i) SEQUENCE CHARACTERISTICS:
        (A) LENGTH: 34 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:23:

Ser Arg Cys Pro His Arg Gly Val Ser Leu Phe Met Gly Arg Val Lys
1               5                   10                  15
Lys Gly Gly Leu Arg Cys Val Tyr His Gly Trp Lys Phe Ser Ala Glu
            20                  25                  30
Gly Lys (2) INFORMATION FOR SEQ ID NO:24:

(i) SEQUENCE CHARACTERISTICS:
        (A) LENGTH: 34 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:24:

Lys Tyr Cys Pro His Arg Arg Val Ser Leu Ile Tyr Gly Arg Asn Lys
1               5                   10                  15
Asn Ser Gly Leu Arg Cys Leu Tyr His Gly Trp Lys Met Asp Val Asp
            20                  25                  30
Gly Asn (2) INFORMATION FOR SEQ ID NO:25:

```
    (i) SEQUENCE CHARACTERISTICS:
        (A) LENGTH: 34 amino acids
        (B) TYPE: amino acid
        (C) STRANDEDNESS:
        (D) TOPOLOGY: linear (ii) MOLECULE TYPE: DNA (genomic)

(xi) SEQUENCE DESCRIPTION: SEQ ID NO:25:

Pro Arg Cys Met His Arg Gly Thr Ser Leu Tyr Tyr Gly His Val Lys
 1               5                  10                  15

Lys Ala Gly Ile Arg Cys Cys Tyr His Gly Trp Leu Phe Ala Val Asp
                20                  25                  30

Gly Thr (2) INFORMATION FOR SEQ ID NO:26:

(i) SEQUENCE CHARACTERISTICS:
        (A) LENGTH: 34 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:26:

Asp Phe Cys Pro His Arg Gly Ala Pro Leu Ser Leu Gly Ser Ile Gln
 1               5                  10                  15

Asp Gly Lys Leu Val Cys Gly Tyr His Gly Leu Val Met Asp Cys Asp
                20                  25                  30

Gly Arg (2) INFORMATION FOR SEQ ID NO:27:

(i) SEQUENCE CHARACTERISTICS:
        (A) LENGTH: 34 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:27:

Gly Tyr Cys Arg His Met Gly Gly Asp Leu Ser Glu Gly Thr Val Lys
 1               5                  10                  15

Gly Asp Glu Val Ala Cys Pro Phe His Asp Trp Arg Trp Gly Gly Asp
                20                  25                  30

Gly Arg (2) INFORMATION FOR SEQ ID NO:28:

(i) SEQUENCE CHARACTERISTICS:
        (A) LENGTH: 35 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:28:

Asp Arg Cys Pro His Arg Leu Ala Pro Leu Ser Glu Gly Arg Ile Asp
 1               5                  10                  15

Glu Thr Gly Cys Leu Gln Cys Ser Tyr His Gly Trp Ser Phe Asp Gly
                20                  25                  30
```

```
Ser Gly Ala
        35

(2) INFORMATION FOR SEQ ID NO:29:

(i) SEQUENCE CHARACTERISTICS:
        (A) LENGTH: 35 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:29:

Asp Leu Cys Pro His Arg Leu Ala Pro Leu Ser Glu Gly Arg Leu Asp
1               5                   10                  15

Glu Asn Gly His Leu Gln Cys Ser Tyr His Gly Trp Ser Phe Gly Gly
            20                  25                  30

Cys Gly Ser
        35

(2) INFORMATION FOR SEQ ID NO:30:

(i) SEQUENCE CHARACTERISTICS:
        (A) LENGTH: 35 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:30:

Asp Gln Cys Pro His Arg Leu Ala Pro Leu Ser Glu Gly Arg Ile Asn
1               5                   10                  15

Lys Ala Gly Gln Leu Glu Cys Pro Tyr His Gly Trp Thr Phe Ala Gly
            20                  25                  30

Ser Gly Gln
        35

(2) INFORMATION FOR SEQ ID NO:31:

(i) SEQUENCE CHARACTERISTICS:
        (A) LENGTH: 34 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:31:

Ser Thr Cys Ala His Arg Ala Cys Pro Leu Asp Leu Gly Thr Val Asn
1               5                   10                  15

Glu Gly Arg Ile Gln Cys Pro Tyr His Gly Trp Glu Tyr Ser Thr Asp
            20                  25                  30

Gly Asn (2) INFORMATION FOR SEQ ID NO:32:

(i) SEQUENCE CHARACTERISTICS:
        (A) LENGTH: 34 amino acids
        (B) TYPE: amino acid
        (C) STRANDEDNESS:
        (D) TOPOLOGY: linear (ii) MOLECULE TYPE: protein
```

```
    (xi) SEQUENCE DESCRIPTION: SEQ ID NO:32:

Asn Thr Cys Ala His Arg Ala Cys Pro Leu His Leu Gly Ser Val Asn
1               5                  10                  15

Glu Gly Arg Ile Gln Cys Pro Tyr His Gly Trp Glu Tyr Ser Thr Asp
            20                  25                  30

Gly Lys (2) INFORMATION FOR SEQ ID NO:33:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:33:

Ala Ala Glu Gln Phe Cys Ser Asp Met Tyr His Ala Ala Thr Met Ser
1               5                  10                  15

His Leu (2) INFORMATION FOR SEQ ID NO:34:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:34:

Ala Ala Glu Gln Phe Cys Ser Asp Met Tyr His Ala Gly Thr Thr Thr
1               5                  10                  15

His Leu (2) INFORMATION FOR SEQ ID NO:35:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:35:

Ala Ala Glu Gln Phe Cys Ser Asp Met Tyr His Ala Gly Thr Met Ala
1               5                  10                  15

His Leu (2) INFORMATION FOR SEQ ID NO:36:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:36:

Ala Ala Glu Gln Phe Cys Ser Asp Met Tyr His Ala Gly Thr Met Ser
```

```
                   1               5                  10                  15
His Leu (2) INFORMATION FOR SEQ ID NO:37:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:37:

Ala Ala Glu Gln Phe Cys Ser Asp Met Tyr His Ala Gly Thr Thr Ser
1               5                  10                  15
His Leu (2) INFORMATION FOR SEQ ID NO:38:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:38:

Ala Ala Glu Gln Phe Cys Ser Asp Ala Tyr His Ala Gly Thr Thr Ser
1               5                  10                  15
His Leu (2) INFORMATION FOR SEQ ID NO:39:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:39:

Ala Ala Glu Gln Phe Cys Ser Asp Met Tyr His Val Gly Thr Thr Ser
1               5                  10                  15
His Leu (2) INFORMATION FOR SEQ ID NO:40:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:40:

Ala Ala Glu Gln Phe Cys Ser Asp Met Tyr His Ala Gly Thr Thr Ser
1               5                  10                  15
His Leu (2) INFORMATION FOR SEQ ID NO:41:
```

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:41:

Thr Ala Glu Asn Gly Ala Asp Gly Tyr His Val Ser Ala Val His Trp
1               5                  10                  15

(2) INFORMATION FOR SEQ ID NO:42:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:42:

Gln Val Glu Asn Cys Ala Asp Gly Tyr His Val Ser Thr Val His Trp
1               5                  10                  15

(2) INFORMATION FOR SEQ ID NO:43:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:43:

Gln Phe Glu Asn Gly Leu Asp Phe Tyr His Phe Gly Ser Thr His Ser
1               5                  10                  15

(2) INFORMATION FOR SEQ ID NO:44:

(i) SEQUENCE CHARACTERISTICS:
        (A) LENGTH: 17 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:44:

Pro Ala Glu Asn Phe Val Gly Asp Ala Tyr His Val Gly Trp Thr His
1               5                  10                  15

Ala (2) INFORMATION FOR SEQ ID NO:45:

(i) SEQUENCE CHARACTERISTICS:
        (A) LENGTH: 17 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:45:

Pro Ala Glu Asn Phe Val Gly Asp Ala Tyr His Val Gly Trp Thr His
1               5                  10                  15

Ala (2) INFORMATION FOR SEQ ID NO:46:

(i) SEQUENCE CHARACTERISTICS:
        (A) LENGTH: 17 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:46:

```
Pro Ala Glu Asn Phe Val Gly Asp Ile Tyr His Ile Gly Trp Thr His
1               5                   10                  15
Ala
```

(2) INFORMATION FOR SEQ ID NO:47:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:47:

```
Gln Ile Glu Asn Gly Ala Asp Gly Tyr His Val Gly Ser Val His Trp
1               5                   10                  15
```

(2) INFORMATION FOR SEQ ID NO:48:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:48:

```
Asn Leu Glu Gly Lys Ile Asp Thr Ser His Phe Asn Pro Leu His Val
1               5                   10                  15
```

(2) INFORMATION FOR SEQ ID NO:49:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:49:

```
Ile Leu Glu Gly Ala Ile Asp Ser Ala His Ser Ser Leu His Ser
1               5                   10                  15
```

(2) INFORMATION FOR SEQ ID NO:50:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:50:

Asn Trp Glu Asn Ile Met Asp Pro Tyr His Val Tyr Ile Leu His Ser
1               5                   10                  15

(2) INFORMATION FOR SEQ ID NO:51:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:51:

Met Ile Asp Asn Leu Met Asp Leu Thr His Glu Thr Tyr Val His Ala
1               5                   10                  15

(2) INFORMATION FOR SEQ ID NO:52:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:52:

Ile Ile Asp Asn Val Thr Asp Met Ala His Phe Phe Tyr Ile His Phe
1               5                   10                  15

(2) INFORMATION FOR SEQ ID NO:53:

(i) SEQUENCE CHARACTERISTICS:
        (A) LENGTH: 17 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:53:

Leu Met Glu Asn Val Ser Asp Pro Ser His Ile Glu Phe Ala His His
1               5                   10                  15
Lys (2) INFORMATION FOR SEQ ID NO:54:

(i) SEQUENCE CHARACTERISTICS:
        (A) LENGTH: 17 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:54:

Leu Met Glu Asn Val Ser Asp Pro Ser His Ile Asp Phe Ala His His
1               5                   10                  15
Lys (2) INFORMATION FOR SEQ ID NO:55:

(i) SEQUENCE CHARACTERISTICS:
        (A) LENGTH: 17 amino acids
        (B) TYPE: amino acid (C) STRANDEDNESS:
        (D) TOPOLOGY: linear (ii) MOLECULE TYPE: protein (xi) SEQUENCE DESCRIPTION: SEQ ID NO:55:

Leu Met Glu Asn Val Leu Asp Ser Ser His Ile Pro Tyr Thr His His
1               5                  10                  15
Lys (2) INFORMATION FOR SEQ ID NO:56:

(i) SEQUENCE CHARACTERISTICS:
        (A) LENGTH: 35 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:56:

Asp Arg Cys Pro His Arg Leu Ala Pro Leu Ser Glu Gly Arg Ile Asp
1               5                  10                  15

Glu Thr Gly Cys Leu Gln Cys Ser Tyr His Gly Trp Ser Pro Asp Gly
                20                  25                  30

Ser Gly Ala
        35

(2) INFORMATION FOR SEQ ID NO:57:

(i) SEQUENCE CHARACTERISTICS:
        (A) LENGTH: 35 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:57:

Asp Leu Cys Pro His Arg Leu Ala Pro Leu Ser Glu Gly Arg Leu Asp
1               5                  10                  15

Glu Asn Gly His Leu Gln Cys Ser Tyr His Gly Trp Ser Pro Gly Gly
                20                  25                  30

Cys Gly Ser
        35

(2) INFORMATION FOR SEQ ID NO:58:

(i) SEQUENCE CHARACTERISTICS:
        (A) LENGTH: 35 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:58:

Asp Gln Cys Pro His Arg Leu Ala Pro Leu Ser Glu Gly Arg Ile Asn
1               5                  10                  15

Lys Ala Gly Gln Leu Lys Cys Pro Tyr His Gly Trp Thr Pro Ala Gly
                20                  25                  30

Ser Gly Gln
        35

(2) INFORMATION FOR SEQ ID NO:59:

(i) SEQUENCE CHARACTERISTICS:
        (A) LENGTH: 17 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:59:

Leu Met Glu Asn Val Ser Asp Pro Ser His Ile Glu Pro Ala His His
1               5                   10                  15

Arg (2) INFORMATION FOR SEQ ID NO:60:

(i) SEQUENCE CHARACTERISTICS:
        (A) LENGTH: 17 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:60:

Leu Met Glu Asn Val Ser Asp Pro Ser His Ile Asp Pro Ala His His
1               5                   10                  15

Arg (2) INFORMATION FOR SEQ ID NO:61:

(i) SEQUENCE CHARACTERISTICS:
        (A) LENGTH: 17 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:61:

Leu Met Glu Asn Val Leu Asp Ser Ser His Ile Pro Tyr Thr His His
1               5                   10                  15

Arg (2) INFORMATION FOR SEQ ID NO:62:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:62:

TGGGGAACTT GATCGCGCAC GCCTTCGG                                    28

(2) INFORMATION FOR SEQ ID NO:63:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid -continued

```
        (A) DESCRIPTION: /desc = "primer"

(xi) SEQUENCE DESCRIPTION: SEQ ID NO:63:

TCGGGCATGG CCTGGGGGAT CTTGG                                              25

(2) INFORMATION FOR SEQ ID NO:64:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "pimer"

(xi) SEQUENCE DESCRIPTION: SEQ ID NO:64:

GGCCACGCGT CGACTAGTAC                                                    20

(2) INFORMATION FOR SEQ ID NO:65:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:65:

GTGCTCGGCT CCGCCTGCTC CGCCGCTTCC CCTGG                                   35
```

What is claimed is:

1. An isolated nucleic acid molecule that encodes a plant protein that suppresses cell death in plants, wherein said nucleic acid molecule comprises a nucleotide sequence having at least 85% identity to the nucleotide sequence set forth in SEQ ID NO:1.

2. An isolated nucleic acid molecule that encodes a plant protein that suppresses cell death in plants, wherein the plant protein comprises the amino acid sequence set forth in SEQ ID NO:2.

3. The nucleic acid molecule of claim 1, wherein said plant protein comprises the carboxy terminal sequence set forth in amino acid residues 261–520 of SEQ ID NO:2.

4. An isolated nucleic acid molecule that encodes a plant protein that suppresses cell death in plants, wherein said nucleic acid molecule comprises the nucleic acid molecule set forth in SEQ ID NO:1.

5. An isolated nucleotide sequence encoding a plant protein that suppresses cell death in plants, wherein said sequence comprises the sequence set forth in SEQ ID NO:4.

6. A chimeric gene comprising the nucleotide sequence of any one of claims 1–4 operably linked to a heterologous promoter.

7. A transformed plant comprising a chimeric gene, said gene comprising a nucledtide sequence which encodes a protein which suppresses plant cell death operably linked to a promoter which is operable in a plant cell, wherein said nucleotide sequence has at least 85% identity to the nucleotide sequence set forth in SEQ ID NO:1.

8. The transformed plant of claim 7, wherein said protein comprises a Rieske iron-coordinating motif.

9. A transformed plant comprising a chimeric gene, said gene comprising a nucleotide sequence that encodes a protein that suppresses plant cell death operably linked to a promoter operable in a plant cell, wherein said protein comprises the amino acid sequence as set forth in SEQ ID NO:2.

10. The transformed plant of claim 7, wherein said protein comprises the carboxy terminal sequence set forth in amino acid residues 261–520 of SEQ ID NO:2.

11. A transformed plant comprising a chimeric gene, said gene comprising a nucleotide sequence that encodes a protein that suppresses plant cell death operably linked to a promoter operable in a plant cell, wherein said nucleotide sequence comprises the sequence set forth in SEQ ID NO:1.

12. Transformed seed from the plant according to any one of claims 7–11.

13. Transformed seed from the plant according to claim 9.

14. Transformed seed from the plant according to claim 10.

15. A method for producing a transgenic plant, said method comprising transforming a plant with an expression cassette comprising a chimeric gene, said gene comprising a nucleotide sequence that encodes a protein that suppresses plant cell death operably linked to a promoter operable in a plant cell, wherein said nucleotide sequence has at least 85% identity to the nucleotide sequence set forth in SEQ ID NO:1.

16. The method of claim 15, wherein said protein comprises a Rieske iron-coordinating motif.

17. A method for producing a transgenic plant, said method comprising transforming a plant with an expression cassette comprising a chimeric gene, said gene comprising a nucleotide sequence operably linked with a promoter operable in a plant cell, wherein said nucleotide sequence encodes the protein set forth in SEQ ID NO:2.

18. The method of claim 15, wherein said protein comprises the carboxy terminal sequence set forth in amino acid residues 261–520 of SEQ ID NO:2.

19. A method for producing a transgenic plant, said method comprising transforming a plant with an expression cassette comprising a chimeric gene, said gene comprising a nucleotide sequence operably linked with a promoter operable in a plant cell, wherein said nucleotide sequence comprises the sequence set forth in SEQ ID NO:1.

* * * * *

UNITED STATES PATENT AND TRADEMARK OFFICE
CERTIFICATE OF CORRECTION

PATENT NO. : 6,211,437 B1
DATED : April 3, 2001
INVENTOR(S) : Briggs et al.

It is certified that error appears in the above-identified patent and that said Letters Patent is hereby corrected as shown below:

Title page,
Item [75], Inventors,
Line 1, "Des Monines" should read -- Des Moines --;
Line 3, "Cork" should read -- Cork City --.

Item [73], Assignee,
Line 3, "Columbus" should read -- Columbia --.

Column 69, claim 7,
Line 59, "nucledtide" should read -- nucleotide --.

Signed and Sealed this

Eleventh Day of December, 2001

Attest:

NICHOLAS P. GODICI
*Attesting Officer*   *Acting Director of the United States Patent and Trademark Office*